(12) United States Patent
Lampropoulos et al.

(10) Patent No.: US 8,118,776 B2
(45) Date of Patent: Feb. 21, 2012

(54) SYSTEM AND METHOD FOR INFLATION SYRINGE WITH IMPROVED DISPLAY AND MODULARIZED COMPONENT ASSEMBLY

(75) Inventors: Fred P. Lampropoulos, Salt Lake City, UT (US); Steve Taylor, Salt Lake City, UT (US); Thomas Stout, Salt Lake City, UT (US); Jim Mottola, Salt Lake City, UT (US); Blaine Johnson, Riverton, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 12/638,631

(22) Filed: Dec. 15, 2009

(65) Prior Publication Data

US 2010/0217188 A1      Aug. 26, 2010

Related U.S. Application Data

(60) Provisional application No. 61/122,708, filed on Dec. 15, 2008.

(51) Int. Cl.
*A61M 29/00* (2006.01)
(52) U.S. Cl. ............................................. 604/97.03
(58) Field of Classification Search .............. 604/97.03, 604/100.01, 100.02, 100.03
See application file for complete search history.

(56) References Cited

U.S. PATENT DOCUMENTS

| | | | |
|---|---|---|---|
| 4,195,637 A * | 4/1980 | Gruntzig et al. | 604/509 |
| 4,370,982 A | 2/1983 | Reilly | |
| D274,470 S * | 6/1984 | Lundquist | D24/114 |
| 4,655,749 A * | 4/1987 | Fischione | 604/97.03 |
| 4,743,230 A * | 5/1988 | Nordquest | 604/97.02 |
| 4,841,977 A | 6/1989 | Griffith et al. | |
| 5,084,060 A | 1/1992 | Freund et al. | |
| 5,135,488 A | 8/1992 | Foote et al. | |
| 5,201,753 A * | 4/1993 | Lampropoulos et al. | 606/192 |
| 5,259,838 A | 11/1993 | Taylor et al. | |
| 5,284,480 A * | 2/1994 | Porter et al. | 604/97.03 |
| 5,300,027 A * | 4/1994 | Foote et al. | 604/100.03 |
| 5,385,549 A * | 1/1995 | Lampropoulos et al. | 604/100.03 |
| 5,425,713 A * | 6/1995 | Taylor et al. | 604/100.03 |
| 5,431,629 A * | 7/1995 | Lampropoulos et al. | 604/100.03 |
| 5,449,344 A * | 9/1995 | Taylor et al. | 604/97.03 |
| 5,449,345 A | 9/1995 | Taylor et al. | |
| 5,453,091 A * | 9/1995 | Taylor et al. | 604/100.03 |

(Continued)

FOREIGN PATENT DOCUMENTS

EP         199083      4/2002

(Continued)

OTHER PUBLICATIONS

International Search Report for PCT/US2009/040310.

(Continued)

*Primary Examiner* — Nicholas Lucchesi
*Assistant Examiner* — Aarti B Berdichevsky
(74) *Attorney, Agent, or Firm* — Stoel Rives LLP

(57) ABSTRACT

An inflation syringe having an improved display and modularized component assembly. More particularly, the present invention relates to methods and apparatuses for providing both numeric and non-numeric indications of an inflation pressurization associated with an inflation syringe. A modularized component assembly for an inflation syringe allowing independent components to be tested independent of the other components of the inflation syringe.

10 Claims, 14 Drawing Sheets

U.S. PATENT DOCUMENTS

| | | | |
|---|---|---|---|
| 5,562,621 A | 10/1996 | Claude et al. | |
| 5,599,301 A * | 2/1997 | Jacobs et al. | 604/65 |
| 5,749,853 A | 5/1998 | O'Donnell et al. | |
| 6,190,354 B1 * | 2/2001 | Sell et al. | 604/96.01 |
| 6,394,977 B1 | 5/2002 | Taylor et al. | |
| 6,533,757 B1 * | 3/2003 | Lampropoulos et al. | 604/131 |
| 7,051,594 B1 | 5/2006 | Aziz | |
| D597,037 S | 7/2009 | Lampropoulos et al. | |
| 7,892,202 B2 * | 2/2011 | Lampropoulos et al. | 604/100.03 |
| 2002/0045854 A1 * | 4/2002 | Royo et al. | 604/97.03 |
| 2004/0193045 A1 | 9/2004 | Scarborough et al. | |
| 2009/0281489 A1 | 11/2009 | Lampropoulos et al. | |

FOREIGN PATENT DOCUMENTS

| | | |
|---|---|---|
| WO | WO2009/137225 | 11/2009 |
| WO | WO2010/075083 | 7/2010 |

OTHER PUBLICATIONS

Office Action dated Dec. 10, 2009 for U.S. Appl. No. 12/118,442.
Response to Office Action filed Apr. 12, 2010 for U.S. Appl. No. 12/118,442.
Office Action dated Jul. 8, 2010 in U.S. Appl. No. 12/118,442.
Notice of Allowance and Fees Due in U.S. Appl. No. 12/118,442.
European Search Report dated Oct. 17, 2011 for PCT/US2009/040310.

* cited by examiner

SYSTEM AND METHOD FOR INFLATION SYRINGE WITH IMPROVED DISPLAY AND MODULARIZED COMPONENT ASSEMBLY

CROSS REFERENCE TO RELATED APPLICATIONS

This application claims the benefit of priority to U.S. Provisional Patent Application No. 61/122,708, filed on Dec. 15, 2008, entitled "Inflation Syringe Display and Modularized Component Assembly," the entire contents of which are incorporated herein by reference.

BACKGROUND OF THE INVENTION

1. The Field of the Invention

Exemplary embodiments of the present invention relates to an inflation device that is used for controlling the inflation of a balloon-tipped catheter. In more particular, the present invention relates to an improved inflation data display that provides an intuitive numeric and non-numeric representation of the inflation pressurization values to facilitate improved monitoring of balloon catheter inflation pressures. The present invention also relates to an improved modularized component assembly system for facilitating assembly of the inflation device apparatus.

2. Background and Relevant Technology

Inflation syringes and catheter technologies have become increasingly important in the interventional radiology and cardiology medical fields. Balloon-tipped catheter systems and inflation syringe apparatus have been utilized in various fields of medicine, such as urology, gynecology, cardiology and others. One area in which balloon-tipped catheter systems and their associated syringe systems have resulted in significant improvement over traditional treatment methods is in connection with the treatment of coronary artery disease.

Coronary artery disease and the associated narrowing of the arteries that feed oxygen-rich blood to the heart (a condition known as "stenosis") is one of the conditions for which balloon-tipped catheters are often utilized as a method of treatment. Traditionally, coronary artery blockages were treated with medicine or by performing coronary artery by-pass surgery. Various kinds of medication could be administered which would decrease the work of the heart by slowing the heart rate, dilating the blood vessels, or lowering blood pressure. However, such medicinal treatments did not cure coronary artery narrowing. As a result, not only would the arterial narrowing remain, but it would also continue to present a risk that at some point the narrowing would become serious enough to require surgical intervention.

In coronary artery by-pass surgery, a blood vessel from the chest or leg is grafted beyond the point of blockage so that the blood detours past the blockage in order to reach the heart. In some severe cases, multiple by-passes are performed. As is well known, coronary artery by-pass surgery is an expensive, highly invasive procedure which often requires prolonged hospitalization and recovery periods.

In the last several years, another method for treating coronary artery disease has developed, called balloon coronary angioplasty, or more technically, percutaneous transluminal coronary angioplasty (PTCA). PTCA is a much less traumatic procedure than coronary artery by-pass surgery. PTCA takes about two hours to perform and can be conducted under local anesthesia. PTCA has significantly improved patient recovery times allowing patients to resume normal activities in a matter of days. Because PTCA is much less expensive and less traumatic than by-pass surgery while still providing effective blockage removal, PTCA has experienced a dramatic increase in the number of such procedures performed each year.

To perform a typical PTCA procedure, an introducer sheath is inserted through an incision made in the groin of the patient or in the artery of an arm of the patient. An x-ray sensitive dye is injected into the coronary artery through a catheter that is introduced through the sheath. The dye enables the doctor, through the use of real-time x-ray technology, to clearly view the patient's vasculature on a television monitor and to thereby locate the blockage. A balloon-tipped catheter is advanced through the vasculature to the point of the blockage with the help of the x-ray monitor.

Due to the increase in the number of PTCA procedures being performed, there has been a substantial increase in the use of electronically monitored inflation syringe systems which are utilized to inflate the balloon catheter or other inflatable balloon-type device during PTCA procedures. Typical syringe systems comprise a barrel and a plunger which are selectively operable to increase fluid pressure applied to the balloon catheter and to remove the applied pressure to the balloon catheter once the procedure is finished. The syringe systems are adapted to provide user readable feedback to the practitioner in the form of a numeric value allowing the practitioner to assess the amount of pressurization that is being applied to the balloon. This allows the practitioner to closely monitor pressurization values to provide a more controlled and systematic inflation of the balloon during the procedure.

Many of the apparatus utilized in PTCA procedures are inexpensive devices which can be discarded after a single use. Disposable devices eliminate expensive and time consuming sterilization procedures which are necessary for reusable devices. Moreover, disposable devices eliminate the risk of transmission of diseases between patients. Consequently designers and manufacturers of inflation syringes have worked to limit the expense of such disposable inflation syringes to make them more cost-effective for a wide variety of applications. As a result, there has been an emphasis in favoring simpler designs over more complex apparatus. Such designs typically comprise a simple digital or analog readout of the inflation pressure on the display provided in connection with the inflation syringes.

Many of the apparatus utilized in PTCA procedures are inexpensive devices which can be discarded after a single use. Disposable devices eliminate expensive and time consuming sterilization procedures which are necessary for reusable devices. Moreover, disposable devices eliminate the risk of transmission of diseases between patients. Consequently designers and manufacturers of inflation syringes have worked to limit the expense of such disposable inflation syringes to make them more cost-effective for a wide variety of applications. As a result, there has been an emphasis in favor simpler designs over more complex apparatus. Such designs typically comprise a simple digital or analog readout of the inflation pressure on the display provided in connection with the inflation syringes.

One typical display of electronically monitored syringes comprises a 7-segment LED display having three to five fields, and perhaps a decimal point. Such simplistic displays are limited in the information they can convey. Some displays provide only the current pressurization of the syringe. Higher-end models may allow the user to toggle the display to view additional information. Although the ability to view additional information can be useful, the user is required to expend mental effort and time to access the additional information, interpret the relevance of the data, and determine how the different values interrelate. Still more expensive syringes may have multiple 7-segment LED displays so as to display multiple values simultaneously. Yet, even with multiple values displayed, a user expends time and mental effort to interpret and relate the values, and to remember which displays represent given values.

BRIEF SUMMARY OF SOME EMBODIMENTS OF THE INVENTION

The present invention relates to an inflation syringe having an improved display and modularized component assembly. More particularly, the present invention relates to methods and apparatus for providing both numeric and non-numeric indications of an inflation pressurization associated with the inflation syringe. According to one embodiment of the present invention, a progressive non-numeric display is provided for displaying the pressurization of the inflation syringe along with numeric indicators of the pressurization.

According to one aspect of the present invention, the progressive display includes a plurality of indicia corresponding to a range of inflation pressurization values. The indicia are actuated to exhibit a given pressurization in a clear and intuitive manner that allows the practitioner to: (1) easily monitor the general intensity of the pressurization; (2) intuitively track changes in the pressurization; and (3) simply observe the relationship of multiple pressurization values without needing to rely solely on more time consuming and less intuitive interpretation of numeric displays. This permits the user to ascertain the relationship between the current pressurization, desired pressurization amounts, and the rate of pressurization in a straightforward and helpful manner.

According to one aspect of the present invention, the display includes a numeric display for representing the pressurization as a numeric value in addition to the non-numeric display. This provides an additional indication of the inflation pressurization that complements the visual indication provided by the non-numeric display. By providing the numeric display and the associated numeric value of the pressurization, a user can identify more minute incremental changes to pressurization and can easily ascertain the precise numeric value of a given pressurization.

The present invention also relates to a method of displaying non-numeric indicia representing inflation pressurization. In the method, a plurality of indicia are provided to signal changes in the inflation pressurization. Once an initial pressurization is indicated, the current pressurization and changes in pressurization can be displayed to the user in a simple and intuitive manner. For example, one or more of the indicia can be actuated as an indication of the current pressurization. In response to a change in the pressurization, a different one of the indicia is actuated to represent the change in pressurization.

According to another aspect of the present invention, the user interface provides one or more desired types of additional data such as a last maximum pressurization value. For example, one or more of the indicia are identified as an indicator of a representative pressurization such as a last maximum pressurization. Once a representative pressurization is indicated such as by illuminating a non-numeric indicia corresponding to such representative pressurization and/or providing a blinking numeric indication of such representative pressurization, the current pressurization and changes in pressurization are displayed to the user in a simple and intuitive manner. For example, once the representative pressurization is indicated, one or more of the indicia can then be actuated as a representation of the current pressurization. In response to a change in the pressurization, a different one of the indicia is actuated to represent the change in pressurization. In one embodiment, the non-numeric indicia of current and representative pressurization values can be shown together allowing the user to simply and intuitively determine the relationship between the two values.

According to one aspect of the present invention, an improved modularized component assembly system, method and process for testing and assembly of the inflation device apparatus is provided. The modularized component assembly enables each component of the inflation device to be tested while also enabling the components to be tested once they have been assembled together. The ability to test individual components and assembled components greatly reduces or altogether eliminates the disposal of functional components or even an entire inflation syringe when a single component of the device is defective. This allows the manufacturer to test individual components separately to assess their viability. As a result, defective components can be readily identified before they are assembled with other components into a functional inflation syringe.

These and other objects and features of the present disclosure will become more fully apparent from the following description and appended claims, or may be learned by the practice of the invention as set forth hereinafter.

BRIEF DESCRIPTION OF THE DRAWINGS

In order to describe the manner in which the above recited and other advantages and features of the invention may be obtained, a more particular description of the invention briefly described above will be rendered by reference to specific embodiments thereof, which are illustrated in accompanying drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF SOME EXEMPLARY EMBODIMENTS

The present invention relates to an inflation syringe having an improved display and modularized component assembly. More particularly, the present invention relates to methods and apparatus for providing both numeric and non-numeric indications of inflation pressurization associated with the inflation syringe. According to one embodiment, a progressive non-numeric display is provided for displaying the pressurization of the inflation syringe along with numeric indicators of the pressurization. The progressive display includes a plurality of indicia corresponding to a range of inflation pressurization values. The indicia are actuated to display a given pressurization and to allow the practitioner to not only easily monitor the general intensity of the pressurization but also to monitor changes in the pressurization without needing to interpret numerical values. This permits the user to quickly ascertain the relationship between the current pressurization, the desired pressurization, and the rate of pressurization.

According to one aspect of the present disclosure, the progressive display includes a numeric display for representing the pressurization as a numeric value. This provides an additional, precise indication of the inflation pressurization that complements the visual indication provided by the non-numeric indicia. According to another aspect of the present invention, a user interface is provided allowing the user to input information that can be used to automatically identify a target pressurization or a last maximum pressurization value. The user interface may also allow the user to select other parameters to be displayed.

A method of displaying a pressurization is also provided according to one aspect of the present invention. In the method, a plurality of indicia adapted to signal changes in the inflation pressurization are provided. One or more of the indicia are identified as an indicator of a desired pressurization such as a last maximum pressurization. Once a desired pressurization is selected, the inflation pressurization is monitored. One or more of the indicia are actuated as an indication of the pressurization. In response to a change in the pressurization, a different one of the indicia is actuated.

An improved modularized component assembly system, and method and process for improving testing, assembly and the cost of the inflation device apparatus, are also provided according to one aspect of the present disclosure. In the method, the components are obtained and then each functional component is tested separately. Once the components have been tested separately, the components are assembled. Consequently, in the event that a single component is defective only the defective component will be discarded, rather than an entire inflation device.

Figure 1:
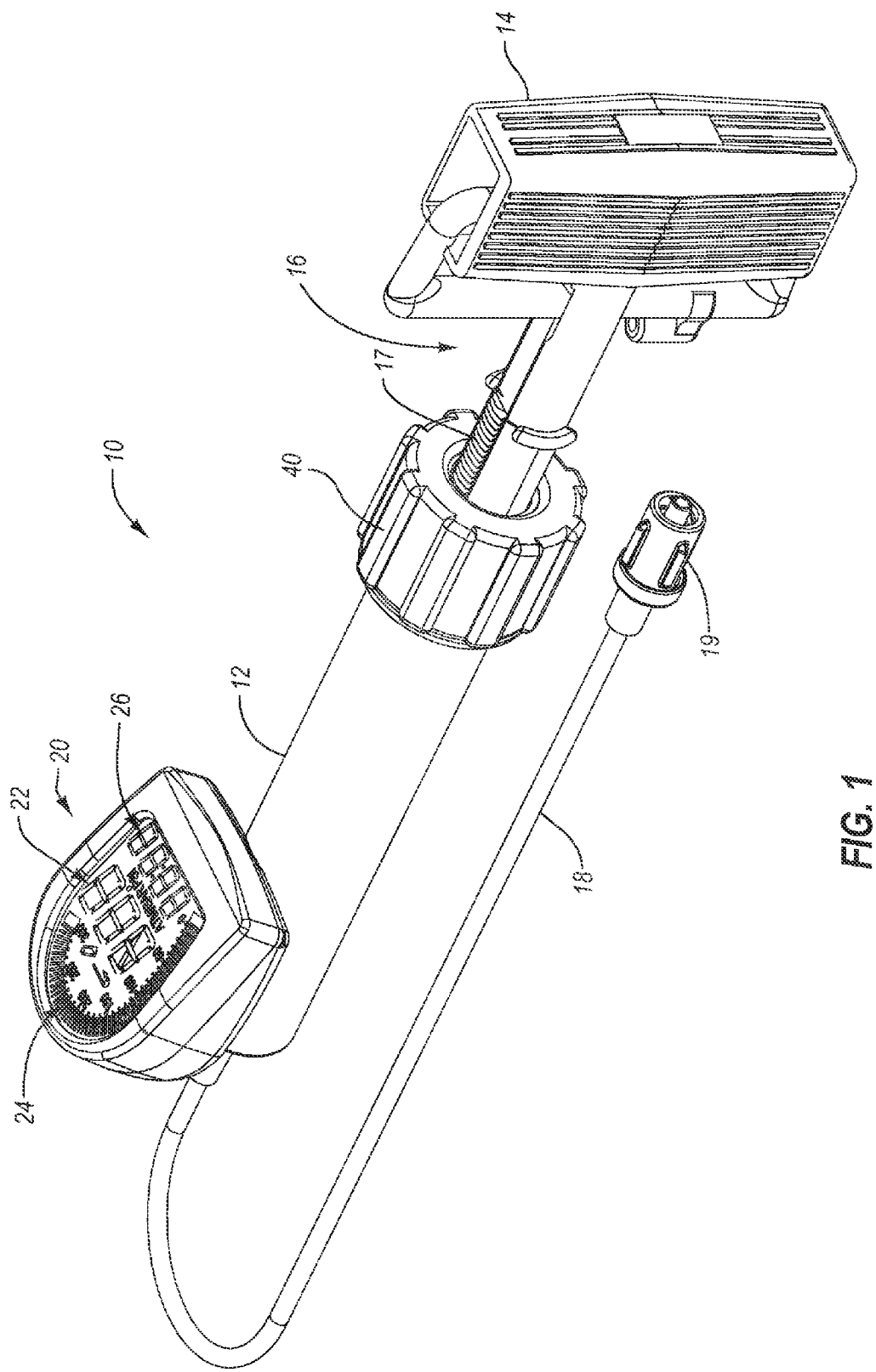
FIG. 1 is a perspective view of an inflation syringe having a display which provides both numeric and non-numeric indicia to represent the pressurization of the inflation syringe.

FIG. 1 illustrates an inflation syringe 10 according to one embodiment of the present invention. Inflation syringe 10 comprises a barrel 12, a plunger 16 and a display 20. Barrel 12 includes an inner lumen which is adapted to hold a pressure transducing medium such as saline or another fluid. Plunger 16 is adapted to increase or decrease the pressurization within barrel 12. Display 20 displays the pressurization information to the user in a simple and intuitive manner.

In the illustrated embodiment, barrel 12 is substantially tubular in configuration. A syringe plunger 16 is configured to be slidably mounted within barrel 12. Plunger 16 includes a threaded portion 17 which is configured to mate with corresponding threads of a plunger retaining nut 40. Plunger retaining nut 40 secures plunger 16 within barrel 12. Tubing 18 is coupled to barrel 12 at one end, and to a rotatable luer coupler 19 at an opposite end. Rotatable luer coupler 19 is adapted to connect tubing 18 to a balloon catheter (not depicted) or another inflatable medical device.

The proximal end of plunger 16 is positioned within the interior of barrel 12 in a fluid-tight manner such that advancing plunger 16 into barrel 12 creates positive pressure within barrel 12. The distal end of plunger 16 comprises a handle 14 which enables a user to apply pressure to push plunger 16 further into barrel 12 or to withdraw plunger 16 from barrel 12. The positive pressure exerted on the fluid contained within barrel 12 is applied to a balloon catheter through tubing 18. Tubing 18 is connected to the balloon catheter by means of a rotatable luer coupler 19. Similarly, by withdrawing plunger 16 toward the rear of the barrel 12, the positive pressure exerted on the balloon catheter may be decreased. According to one embodiment of the present invention, the process of pressurizing barrel 12 to a desired pressurization and then depressurizing barrel 12 can be considered an inflation routine.

In the illustrated embodiment, a display 20 is mounted to the exterior of barrel 12. Display 20 provides an intuitive and easy to read configuration. In the illustrated embodiment, display 20 includes a numeric display 22, non-numeric display 24, and a timer display module 26. By providing both a numeric display 22 and non-numeric display 24, display 20 allows a user to read and understand a wider variety of information than provided by existing displays. Additionally, display 20 provides pressurization information in a helpful and intuitive manner eliminating the time and mental effort required for a user to interpret the output of existing displays. In this manner, a practitioner can focus on other aspects of the procedure to be performed without needing to focus on interpreting individual numeric or other information provided by existing displays.

In the illustrated embodiment, display 20 is coupled to a pressure sensing apparatus such as a pressure transducer. The pressure sensing apparatus may be integrated within the wall of barrel 12, mounted within barrel 12, positioned in fluid communication with the interior of barrel 12, or otherwise configured to detect the pressure inside barrel 12. As used to describe the relationship of the pressure sensing apparatus and the interior of barrel 12, the term "fluid communication" may include pneumatic or hydraulic transmission (direct or indirect) of fluid pressures exerted within barrel 12 and tubing 18 to the pressure sensing apparatus so that such fluid pressures can be sensed by the pressure sensing apparatus. Direct transmission of such fluid pressures can be provided, for example, by means of a diaphragm of a piezoresistive semiconductor transducer which is placed into contact (either pneumatically or hydraulically, or a combination of both) with a fluid contained in a closed system. Indirect transmission can occur, for example, where the transducer means is coupled to a diaphragm that in turn contacts the fluid contained in a closed system.

The pressure sensing apparatus may be coupled to display 20 on the exterior of barrel 12 so as to communicate pressurization information associated with the interior of barrel 12. In another embodiment, the pressure sensing apparatus may be integrated with display 20 and in fluid communication with the interior of barrel 12, so as to detect pressurization within barrel 12. In one embodiment, a pressure sensing apparatus is located at the end of connecting tubing attached through a T-connector to tubing 18. Alternatively, the pressure sensing apparatus can be mounted as part of the electronic circuitry contained inside of display 20. In yet another embodiment, the pressure sensing apparatus is located at another position remote from the barrel 12. The pressure sensing apparatus can comprise a piezoresistive semiconductor type transducer. In still another embodiment the pressure sensing apparatus may comprise transducer apparatus other than a piezoresistive or semiconductor apparatus. For example, in one embodiment the pressure sensing apparatus comprises a conventional strain gauge transducer, which has been known and used in the art for many kinds of different pressure monitoring applications, or fiberoptic transducers.

As will be appreciated by those skilled in the art, a variety of types and definitions of inflation routines can be utilized without limiting the scope of the invention. By way of example, and not by limitation, an inflation routine may begin when pressurization of barrel 12 begins, and can include several instances of advancing plunger 16 within barrel 12 and retracting plunger 16 from barrel 12. The inflation routine may end when all pressure is released from barrel 12. In another exemplary embodiment, an inflation routine may begin when positive pressurization is exerted within barrel 12 and ends at the conclusion of a first period of depressurization of the barrel. In one embodiment, not all of the pressurization may be released from barrel 12 at the end of the first period of depressurization. Thus, if not all pressure is released from barrel 12, the next inflation routine may begin when an increase in pressurization is again detected, even where the pressurization is at a lower value than the maximum pressurization value of the previous inflation routine. Additionally, an inflation routine may be utilized with a pressurization mechanism other than an inflation syringe.

As will be appreciated by those skilled in the art, the function of inflation syringe 10 can be provided by a variety of syringe or pressurization systems, without departing from the scope and spirit of the present invention. In one embodiment, a pump device that is pressurized by a plunger or similarly functioning component that is actuated multiple times, and that releases the pressure through a valve is utilized instead of a barrel and plunger syringe system. In another embodiment an automatic pressurization device may provide the required pressure to a tubing and the pressure in the tubing may be detected and monitored. A more complete description of one embodiment of a syringe system is contained in U.S. Pat. No. 5,057,078.

Figure 2:
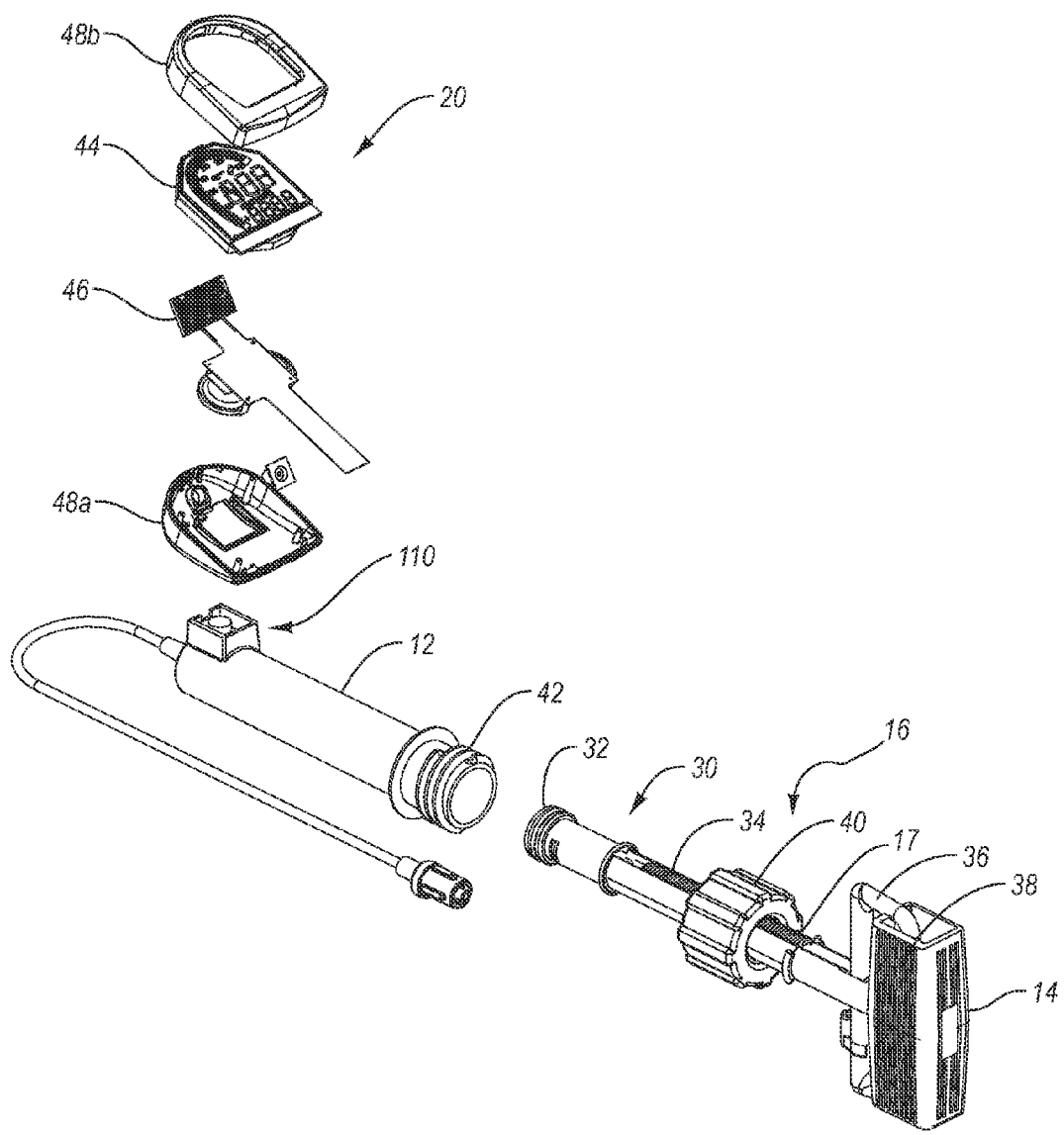
FIG. 2 is an exploded view of the inflation syringe of FIG. 1 illustrating the components of the inflation syringe and the modularized component assembly of the inflation syringe.

FIG. 2 is an exploded view of inflation syringe 10 of FIG. 1, illustrating the components of inflation syringe 10 and the modularized component assembly of inflation syringe 10. In the illustrated embodiment, plunger 16 and handle 14 are shown separately from barrel 12. Plunger 16 comprises a proximal end 30, a rubber tip 32 and threads 34. The distal end of plunger 16 includes a handle receiving component 38 and a spring-activated trigger 36.

In the illustrated embodiment, rubber tip 32 is positioned at proximal end 30 of plunger 16. Rubber tip 32 is adapted to engage the interior of barrel 12 in a fluid-tight manner to allow the user to increase the pressurization on fluid positioned within barrel 12. As the user advances plunger 16 further into barrel 12, rubber tip 32 is also advanced to increase the positive pressure within barrel 12. Similarly, the user can retract plunger 16 in a rearward direction within barrel 12 to decrease the pressurization within barrel 12.

In the illustrated embodiment, plunger 16 is secured within barrel 12 by plunger retaining nut 40. The configuration of retaining nut 40 allows a user to secure plunger 16 within barrel 12 by threadably coupling retaining nut 40 to barrel securement threads 42. The configuration of retaining nut 40 secures plunger 16 within barrel 12 while allowing for slidable movement of plunger 16 in forward and rearward directions within barrel 12. In the illustrated embodiment, barrel securement threads 42 are adapted to cooperatively engage one or more additional components of inflation syringe 10. For example, barrel securement threads 42 can be adapted to mate with a second set of corresponding threads integrated within plunger retaining nut 40.

The distal end of plunger 16 includes a handle receiving component 38 which is configured to accept and engage a spring-activated trigger 36. In the illustrated embodiment, a user can advance syringe plunger 16 without engagement of threads 17 by actuating spring-activated trigger 36. When the user actuates spring-activated trigger 36, a portion of trigger 36 is retracted into handle receiving component 38. Retracting spring activated trigger 36 into handle receiving component 38 disengages threads 34 from the corresponding threads of plunger retaining nut 40. As a result, plunger 16 can freely slide in either a proximal direction or distal direction within barrel 12. By releasing the compression on trigger 36 relative to handle receiving component 38, the threads 34 are then permitted to engage the corresponding threads of plunger retaining nut 40. Engagement between threads 34 and plunger retaining nut 40 allows plunger 24 to be advanced or retracted by screwing plunger 16 either in a clockwise or counter clockwise direction respectively.

Trigger 36 allows the user to rapidly provide an increase or decrease of pressurization within barrel 12 of inflation syringe 10. In other words, a user can compress trigger 36 against handle receiving component 38 and threadlessly advance or retract plunger 16 within barrel 12 to increase or decrease the pressurization within barrel 12. The user can then release trigger 36 and threadably advance or retract plunger 16 within barrel 12 to provide a more gradual adjustment of plunger 16 to a more exacting desired pressurization. Additionally, threadably advancing plunger 16 within barrel 12 can be utilized to provide greater pressurization within barrel 12 than can be accomplished by threadless advancement alone.

In the illustrated embodiment, the body of syringe barrel 12 includes a mounting bracket 110. Mounting bracket 110 provides a mechanism for securing display 20 to syringe barrel 12. Mounting bracket 110 is integrally coupled to the proximal, or leading end, of barrel 12. In the illustrated embodiment, mounting bracket 110 is in fluid communication with the interior of barrel 12 through an opening (not depicted)

formed in the sidewall of barrel 12 for the purpose of communicating pressurization information from the interior of barrel 12.

In the illustrated embodiment a display 20 is provided to relate pressurization information to a user. Display 20 includes a display module 44, display circuitry 46, and a housing 48. Display circuitry 46 is adapted to be coupled to display module 44. Display circuitry 46 provides the pressurization and other information to be shown by display module 44. Housing 48 comprises a housing base 48b and a housing hood 48a. Housing base 48b is adapted to receive display circuitry 46 and display module 44. Housing hood 48a can then be secured to housing base to secure display circuitry 46 and display module 44 within housing 48. Housing hood 48a is adapted to secure display module 44 such that it is viewable to a user.

By providing modularized components such as display module 44, display circuitry 46, and housing 48, in connection with display 20, a manufacturer can simply and efficiently assemble the components of display 20. Additionally, by utilizing modularized components in connection with display 20 a manufacturer can independently test of each component of display 20, before assembly and/or attachment to a syringe system or other inflation device. In this manner, in the event that a single component of display 20, such as display circuitry 46, is defective, the manufacturer can identify the defective component before assembly of display 20. This allows the user to discard the defective individual component without discarding the entire display including non-defective components of display 20 and/or inflation syringe 10. A method of modularized component assembly is discussed more fully below in conjunction with the discussion of FIGS. 6 and 7.

In the illustrated embodiment, display module 44 may comprise a numeric indicia, non-numeric indicia, and/or a timer display module. By providing numeric and non-numeric indicia, a simple and intuitive display of pressurization information can be provided to a user. Display module 44 is an example of a means for displaying inflation pressurization information. Display circuitry 46 processes electrical signals representing pressurization information that are output by a pressure sensing apparatus. Display circuitry 46 can also control the manner in which the display module 44 displays the pressurization information. Display circuitry 46 is provided as an example of a means for processing electrical signals from a sensor apparatus. Other examples of a means for processing electrical signals can include, but are not limited to, a microchip, a personal computer, and a handheld device such as a personal digital assistant (PDA). A method of displaying pressurization information using numeric indicia and non-numeric indicia is discussed below in conjunction with the discussion of FIGS. 4 and 5.

According to one aspect of the present invention, display 20 may further include a pressure sensing apparatus. The pressure sensing apparatus is positioned in fluid communication with the interior of barrel 12. In the illustrated embodiment, the pressure sensing apparatus is integrated with display circuitry 46. Display circuitry 46 and the pressure sensing apparatus of display circuitry 46 is positioned in fluid communication with the interior of barrel 12.

As will be appreciated by those skilled in the art, a variety of types and configurations of displays can be utilized without departing from the scope and spirit of the present invention. According to one embodiment of the present invention, the display is provided separately from the inflation syringe. For example, the display can be provided as part of a reusable user interface which is operably connected to a disposable inflation syringe. Other examples of means for displaying inflation pressurization can also be utilized including, but not limited to, a cathode ray tube display, a liquid crystal display (LCD) screen, a grouping of light emitting diodes (LEDs), a handheld device such as a personal digital assistance (PDA), and a printer for printing out a hard copy display.

Figure 3A:
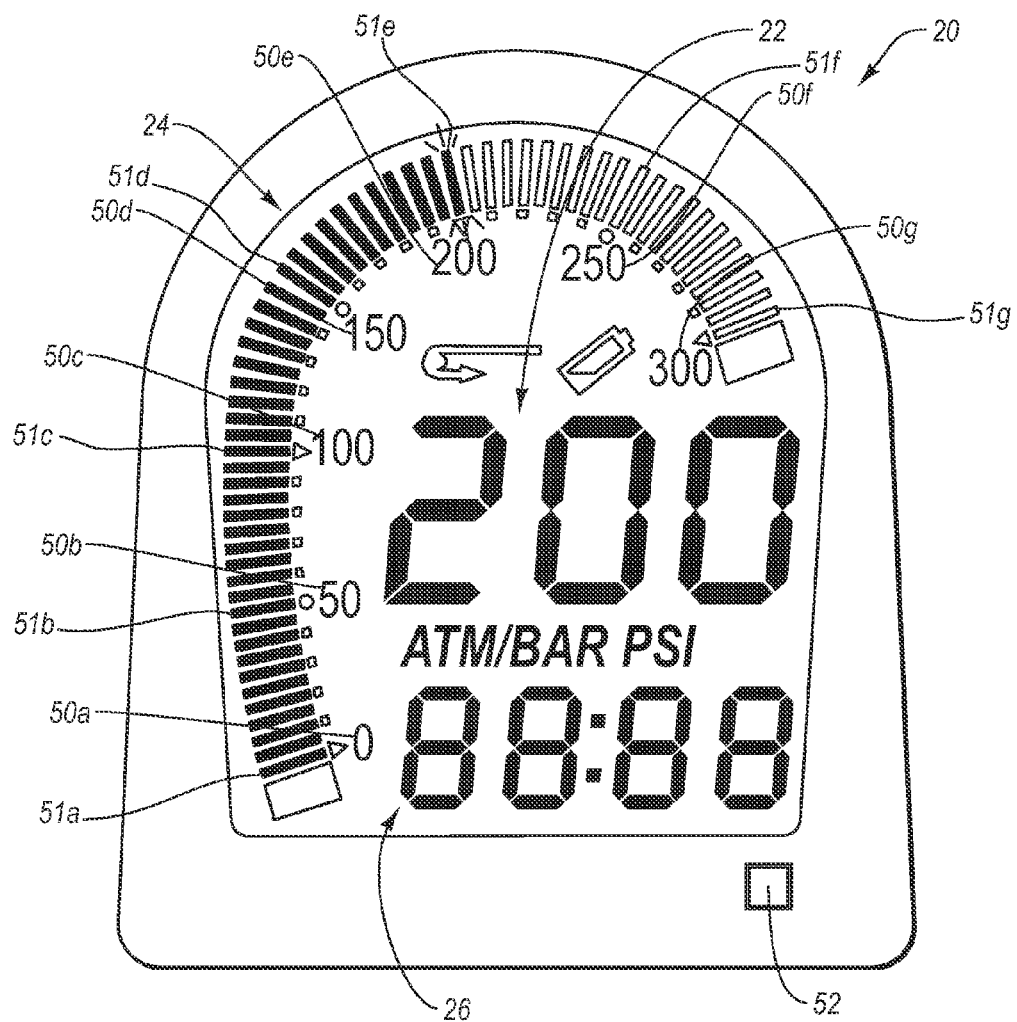
FIG. 3A illustrates a display of an inflation syringe comprising numeric and non-numeric indicia displaying the current pressurization of the inflation syringe

FIGS. 3A through 3D depict a display 20 having numeric and non-numeric indicia for displaying pressurization information to a user in a simple and intuitive manner according to one aspect of the present invention. With reference now to FIG. 3A, in the illustrated embodiment, display 20 includes a non-numeric display 24 and numeric display 22. Non-numeric display 24 comprises a plurality of indicia 51. Indicia 51 are configured to provide a progressive display which depicts the pressurization of the inflation syringe in a simple and intuitive manner. The progressive configuration of display and corresponding indicia 51 can provide an indication of a range of inflation pressurization values. As indicia 51 are actuated, the user can quickly and simply determine the pressurization of the inflation syringe 10 allowing the practitioner to not only easily monitor the general intensity of the pressurization but also to monitor changes in the pressurization without needing to interpret numerical values. As a result, the user can quickly ascertain the relationship between the current pressurization, the desired pressurization, and the rate of pressurization without needing to interpret numeric values. In one embodiment, alternative measurements values other than pounds per square inch (psi), such as atmospheres or bar are provided.

In the illustrated embodiment, numeric display 22 of display 20 provides a numeric indication of the pressurization in the inflation syringe. Numeric display 22 provides an additional, precise indication of the inflation pressurization that complements the visual indication provided by the non-numeric indicia 51. In the illustrated embodiment, numeric display 22 comprises a digital display, such as a 7-segment LED display having multiple fields. As depicted, numeric display 22 includes three fields, each field representing a digit of the numeric value. Numeric display 22 displays a current pressurization value.

In the illustrated embodiment, display 20 may further comprise a timer display module 26. Timer display module 26 provides an indication of the length of an inflation routine, the length of time between inflation routines, the length of time at a particular pressurization value, and/or the length of time that inflation pressure is applied to an attached inflatable medical device. Display 20 may also include a last value actuation button 52. Last value actuation button 52 allows a user to toggle the numeric display 22 to display the maximum pressurization value achieved during the most recent, or previous, inflation routine.

In the illustrated embodiment, an exemplary current pressurization value of the inflation syringe is displayed as 200 pounds per square inch (psi). The numeric display 22 is configured to provide a precise, intuitive indication of a value, which typically is the current pressurization of the interior of barrel 12. During an inflation routine, numeric display 22 is automatically updated in real-time to provide the practitioner with an immediate, intuitive indication of the pressurization within the interior of the barrel and/or the tubing of the inflation syringe. The depicted 7-segment LED display is provided as an exemplary display capable of providing a straight-forward and easy-to-read, digital display at a low cost.

As previously discussed, in the illustrated embodiment non-numeric display 24 includes a plurality of non-numeric indicia 51. Each of non-numeric indicia 51 comprises a white or colored LED. Additionally, each of the plurality of non-numeric indicia 51 of the non-numeric display 24 can represent one or more pressurization values. A plurality of numeric value indicators 50 are provided in connection with indicia 51 to provide a representation of the pressurization values corresponding to one, or a group of, non-numeric indicia 51.

In the illustrated embodiment, each indicia 51 represents a range of pressurization values corresponding to approximately five psi. The numeric value indicators 50*a, b, c, d*, e, f, g are spaced along the indicia 51, as shown, with a numeric value indicator corresponding with every tenth indicia 51. As a result, the numeric value indicator 50*a* which is labeled as "0" clearly illustrates to the user than when no indicia is illuminated, or when indicia 51*a* alone is illuminated, the pressurization within the inflation syringe is zero psi.

An exemplary non-numeric indicia 51*b* is also depicted. In the illustrated embodiment, indicia 51*b* is positioned approximately ten non-numeric indicia from indicia 51*a*. A numeric value indicator 50*b* which is labeled "50" is provided in connection with indicia 51*b* representing a pressurization within the inflation syringe of fifty psi. As a result, when the indicia from 50*a* to 50*b* are illuminated, the user can quickly and simply determine that the pressurization within the inflation syringe is fifty psi.

As will be appreciated by those skilled in the art, when the pressurization within the inflation syringe is between zero psi and fifty psi, one of the non-numeric indicia 51 positioned between indicia 51*a* and 51*b* will be illuminated as the non-numeric representation of the pressurization within the inflation syringe. For example, in the event that the pressurization within the inflation syringe is 35 psi, approximately 7 non-numeric indicia will be illuminated due to the fact that each non-numeric indicia represents a range of five psi of pressurization. In the event that the pressurization within the inflation syringe is 45 psi, approximately 9 non-numeric indicia will be illuminated. The user can quickly ascertain the approximate pressurization within the inflation syringe by how close the last illuminated indicia is to a particular numeric value indicator. For example, when the pressurization in the inflation syringe is 35 psi, the user can quickly identify that the last illuminated non-numeric indicia is greater than zero psi, less than 50 psi. Additionally, the user can quickly identify that the last illuminated non-numeric indicia is closer to 50 psi than 0 psi. As a result, the non-numeric display 24 allows a user to quickly determine the approximate pressurization within the inflation syringe.

In the illustrated embodiment, numeric value indicator 50*c* indicates that an indicia 51*c* corresponds with a pressurization value of 100 psi. Numeric indicators 50*d* through 50*g* are similarly spaced, and respectively indicate that indicia 51*d*, 51*e*, 51*f* and 51*g* represent pressurization values 150 psi, 200 psi, 250 psi, and 300 psi, respectively. In the illustrated embodiment, non-numeric indicia 51 are lit in a progressive manner. Thus, all non-numeric indicia 51 representing values less than the current pressurization value remain lit as the pressurization increases and additional non-numeric indicia 51 are illuminated.

Figure 3B:
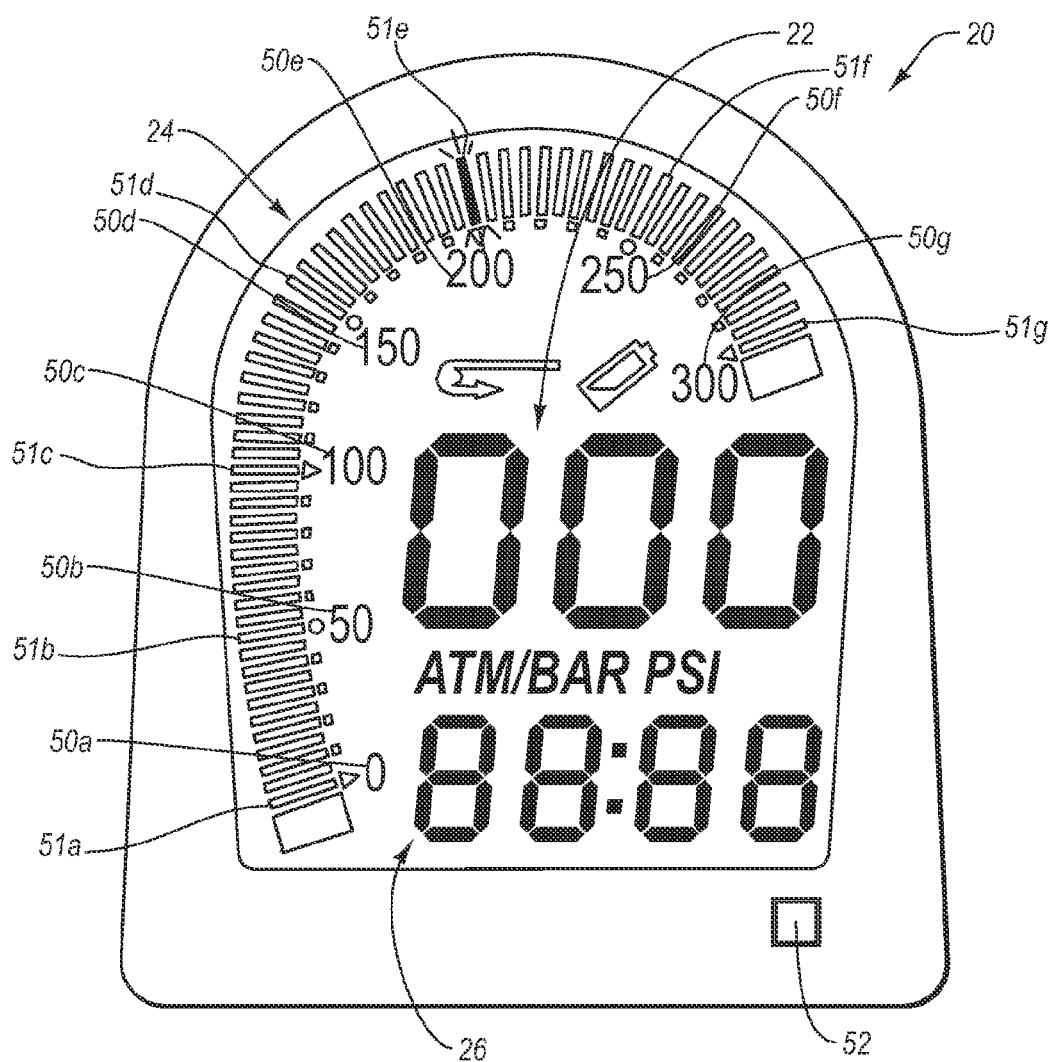
FIG. 3B illustrates the display of the inflation syringe in which last pressurization value information is displayed to a user utilizing non-numeric indicia.

FIG. 3B illustrates a display 20 subsequent to previous pressurization routine of the inflation syringe. In the illustrated embodiment, there is little or no pressurization within the inflation syringe. As a result, numeric display 22 shows a pressurization of zero psi. Additionally, non-numeric indicia 51*a*-51*b* are not illuminated.

In the illustrated embodiment, a non-numeric indicia 51*e* is illuminated. Non-numeric indicia 51 is illuminated as a representation of a value that represents something other than the current pressurization of the inflation syringe. According to one embodiment of the present invention, an indicia 51, such as non-numeric indicia 51*e*, can be lit to represent a last pressurization value and/or a target pressurization value. To avoid confusion, an indicia 51 representing a last value and/or a target value may appear a different color and/or flash or blink. In the illustrated embodiment, it is fairly simple to ascertain that non-numeric indicia 51 represents a last pressurization value and not the current pressurization value as the indicia between 51*a* and 51*e* are not illuminated. As will be appreciated by those skilled in the art, a non-numeric indicia can be illuminated as an indicator of a last pressurization value while current pressurization is also be illuminated.

Display 20 may further comprise a user interface which allows a user to set a target pressurization value different from the last value. This may be accomplished by adjusting up or down from the displayed last pressurization value, or by manually entering a target value. In still another embodiment, last value actuation button 53 can enable the toggling of numeric display 22 between three values, current pressurization, last value, and target value. The target value may also be indicated by the non-numeric display 24, either with the last value or in place of the last value, thus giving a user a visual representation of progress made in pressurizing the barrel, how much progress remains to reach the last value or a desired value, the rate of pressurization, and changes in pressurization resulting from each movement of the plunger within the barrel. Thus, the user can more easily ascertain the force necessary for subsequent movements of the plunger to reach the target pressurization value. The user interface may also enable the user to select other parameters to be displayed.

Figure 3C:
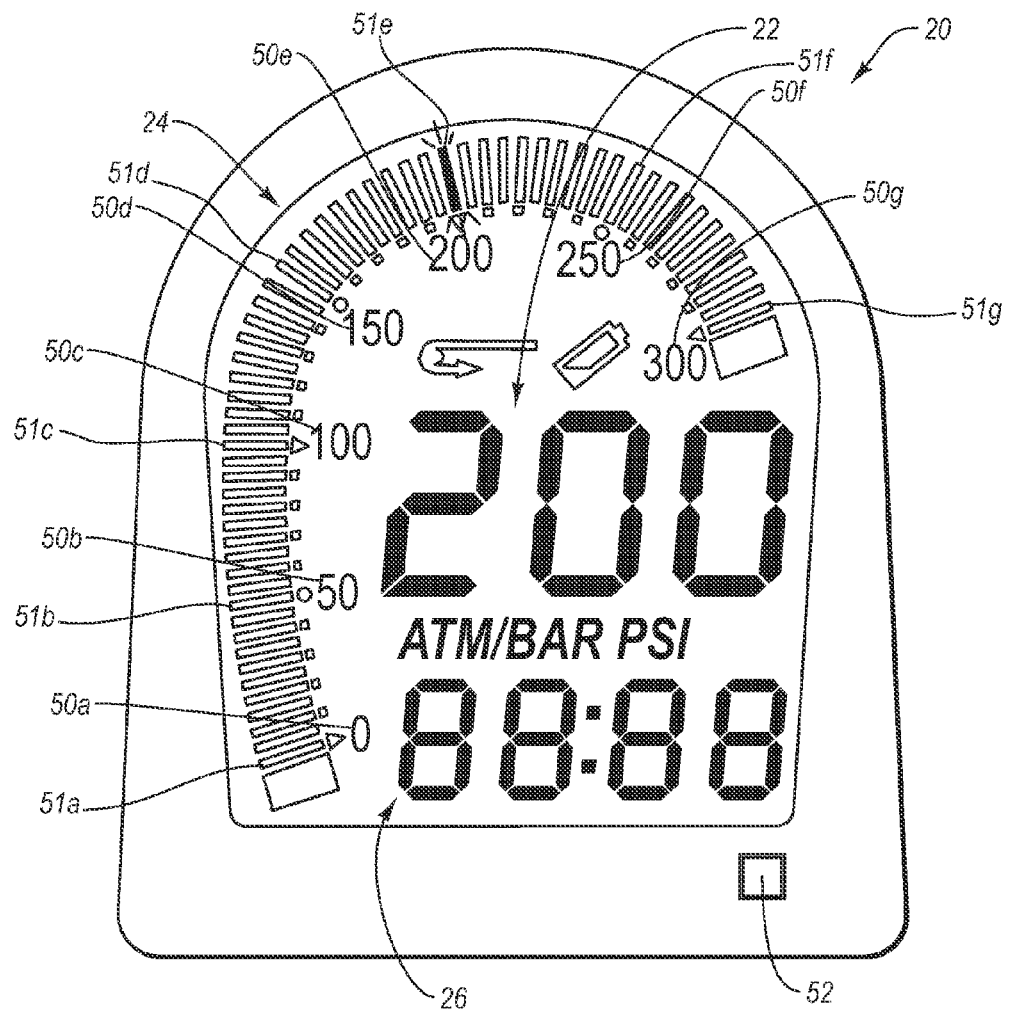
FIG. 3C illustrates the display of the inflation syringe in which last value information is displayed to a user utilizing both numeric and non-numeric indicia.

FIG. 3C depicts display 20 of FIGS. 3A and 3B showing another manner of displaying last value information to a user, immediately after the user has pressed the last value actuation button 52. In FIG. 3B, the barrel of the inflation syringe is completely depressurized, as indicated by numeric display 22 and non-numeric display 24. If the user wants to view the exact last pressurization value, this information is not readily represented by indicia 51*e* because of the multiple possible pressurization values represented by each indicia 51. To view the precise last pressurization value, the user can toggle the display by pressing last value actuation button 52. In the illustrated embodiment, the user has pressed the last value actuation button 52. Both indicia 51*e* of non-numeric display 24 and the 7-segment display of numeric display 22 indicate the last value is 200 psi. By displaying the last value pressurization information on non-numeric display 24 and numeric display 22, precise pressurization information is provided to a user in intuitive and easy to read manner.

In one embodiment of the present invention, display 20 may automatically toggle to display last value information at the end of an inflation routine. In the embodiment, display 20 will continue to display last value information on both the numeric display 22 and non-numeric display 24 until the beginning of the next inflation routine. At the beginning of the next inflation routine, display 20 may automatically toggle back to display current pressurization value information on numeric display 22 while retaining last value information using non-numeric display 24. According to one embodiment of the present invention the precise last value information may be available by pressing last value actuation button 52 at any time including during or subsequent to a pressurization routine. Indicia 51*e* may appear as a different color and/or flash to indicate it is presently representing a last value. In another embodiment, a user may adjust which indicia is appearing in a different color and/or which indicia is flashing while setting a target value which is different from the last pressurization value.

Figure 3D:
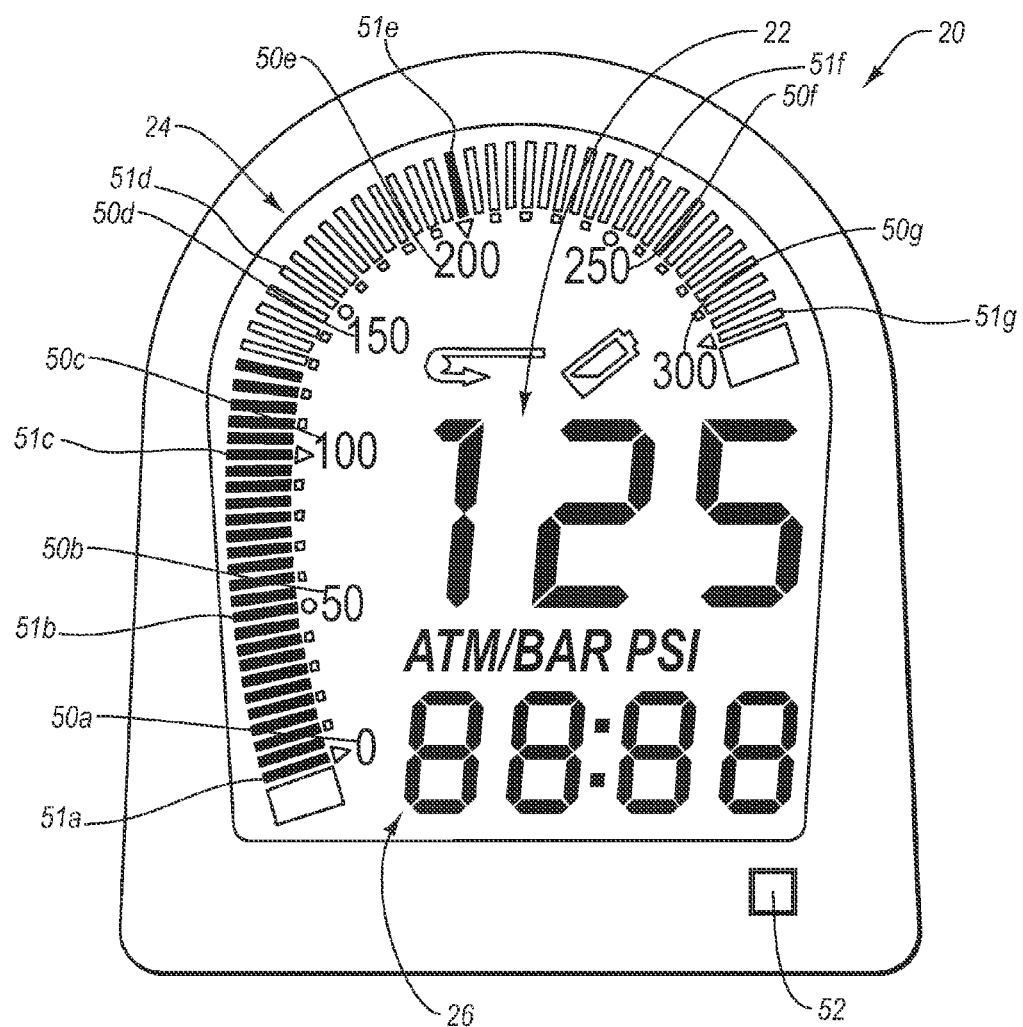
FIG. 3D illustrates the display of the inflation syringe demonstrating operation of the display during re-pressurization of the inflation syringe.

FIG. 3D illustrates display 20 during a subsequent pressurization routine in which the current pressurization of the inflation syringe is provided simultaneously with the last pressurization value. In the illustrated embodiment, non-numeric indicia 51e is illuminated as an indicator of the last pressurization value. In other words, non-numeric indicia 51e allows a user to quickly determine the maximum pressurization of the inflation syringe during the preceding inflation routine. Because non-numeric indicia 51e corresponds with an exemplary pressurization value of 200 psi, the user can quickly determine that a maximum pressurization of 200 psi was utilized during the previous pressurization routine. This may be helpful where a practitioner desires to apply a similar, lesser or greater pressurization during subsequent pressurization routines. The configuration of display 20 allows a user to quickly ascertain the present pressurization value, the progress made and remaining to reach the last value and/or the target pressurization value, the rate of pressurization, and the progress made with each movement of the plunger, in a intuitive and simple to read manner.

In the illustrated embodiment, indicia 51a through 51c are illuminated. Additionally, approximately 5 additional indicia positioned between indicia 51c and 51d are illuminated. Because indicia 51c represents a pressurization of 100 psi, the user can quickly and simply ascertain that the pressurization in the inflation syringe represents a pressurization which is greater than 100 psi. Additionally, due to the fact that indicia 51 corresponds with a pressurization of 150 psi, the user can quickly ascertain that the current pressurization in the inflation syringes represents a pressurization that is less than 150 psi. Due to the progressive nature of non-numeric indicia 51 and non-numeric display 24, the user can visually determine that the pressurization is approximately 125 psi due to the fact that the last illuminated non-numeric indicia 51 is positioned approximately midway between 100 psi and 150 psi. This can be quickly confirmed by simply glancing at numeric indicia 22 which confirms that the pressurization in inflation syringe is exactly 125 psi.

Providing a non-numeric display 24 in connection with a numeric display 22 provides an intuitive and simple to read display while also displaying more information simultaneously on the display than can be depicted on a numeric display alone. For example, the numeric display 22 can provide a current pressurization value while the non-numeric display 24 simultaneously displays a current pressurization value and a last pressurization value. In the illustrated embodiment, the user can determine the approximate pressurization of the inflation syringe utilizing the non-numeric display 24. Additionally, the user can quickly and easily identify the relationship between the current pressurization and a target or last pressurization value. Additionally, the non-numeric display 24 can provide a visual representation of progress previously made in pressurizing the barrel, and of how much additional pressurization in needed to reach a desired value, such as the last pressurization value or a target pressurization value. For example, the user is provided with a visual indication that the current pressurization of 125 psi is approximately two-thirds of the last pressurization value represented by non-numeric indicia 51e. Additionally, the user can quickly ascertain that the current pressurization is slightly less than half of a maximum pressurization of 300 psi which corresponds with a non-numeric indicia 51g.

Display 20 also allows a user to easily monitor the rate of pressurization and changes in pressurization resulting from each movement of the plunger within the barrel. Thus, the user can more quickly estimate the force necessary for subsequent movements of the plunger to reach a desired pressurization value. In the illustrated embodiment, the arcuate or curved configuration of non-numeric display 24 allows a user to determine progress along a pressurization curve. The configuration of the pressurization curve provides subtle non-numeric indications in addition to actual pressurization values. For example, pressurizations corresponding with the bottom portion of the curve, i.e. indicia 51a-51c, can quickly be identified as below typically desired maximum pressurization values. As the pressurization approaches the arch or apex of the curve, i.e. indicia 51d-51f, the user can ascertain that the pressurization is within a range of typically desired maximum pressurization values. As the user passes the apex of the curve and begins to descend toward the final non-numeric indicia, i.e. 51f-51g, the user can quickly determine that the pressurization exceeds typically desired maximum pressurization values. In this manner, the shape of the non-numeric indicia provides an indication of the desirability of given pressurization values in addition to actual pressurization values.

As will be appreciated by those skilled in the art, a variety of types and configurations of non-numeric displays can be provided without departing from the scope and spirit of the present invention. For example, a non-numeric display can comprise a progressive wage gauge or dial. In one example, the dial may be digital, comprising indicated by lights (e.g. LEDs), changing colors, notches, and/or other indicia. In another embodiment, rather than comprising a digital gauge or dial, non-numeric display may comprise an analog dial, such as an arm configured to pivot in an arc, moving along increments positioned in a curvilinear fashion on a portion of the arc. In still another embodiment, non-numeric display may comprise an analog gauge that displays a representation of current pressurization and progress of pressurization along a range of possible inflation pressures. According to one embodiment of the present invention, the non-numeric display may comprise indicia arranged in a linear or curvilinear array. In still another embodiment there may be a plurality of instances of non-numeric indicia, each instance representing different pressurization values (e.g. current pressurization and last value). In still another embodiment the non-numeric indicia may be arranged in a non-linear configuration. In the illustrated embodiment, one side of the arcuate curve is longer than the other side of the curve to represent the respective desired ranges of values previously referenced.

According to an alternative embodiment of the present invention, different colors of pressurization can be provided as the pressurization increases along the pressure curve. For example, at low pressurization, the non-numeric indicia are illuminated green. At medium pressurization, the non-numeric indicia are illuminated yellow. At high pressurizations, the non-numeric indicia are illuminated red.

Figure 4:
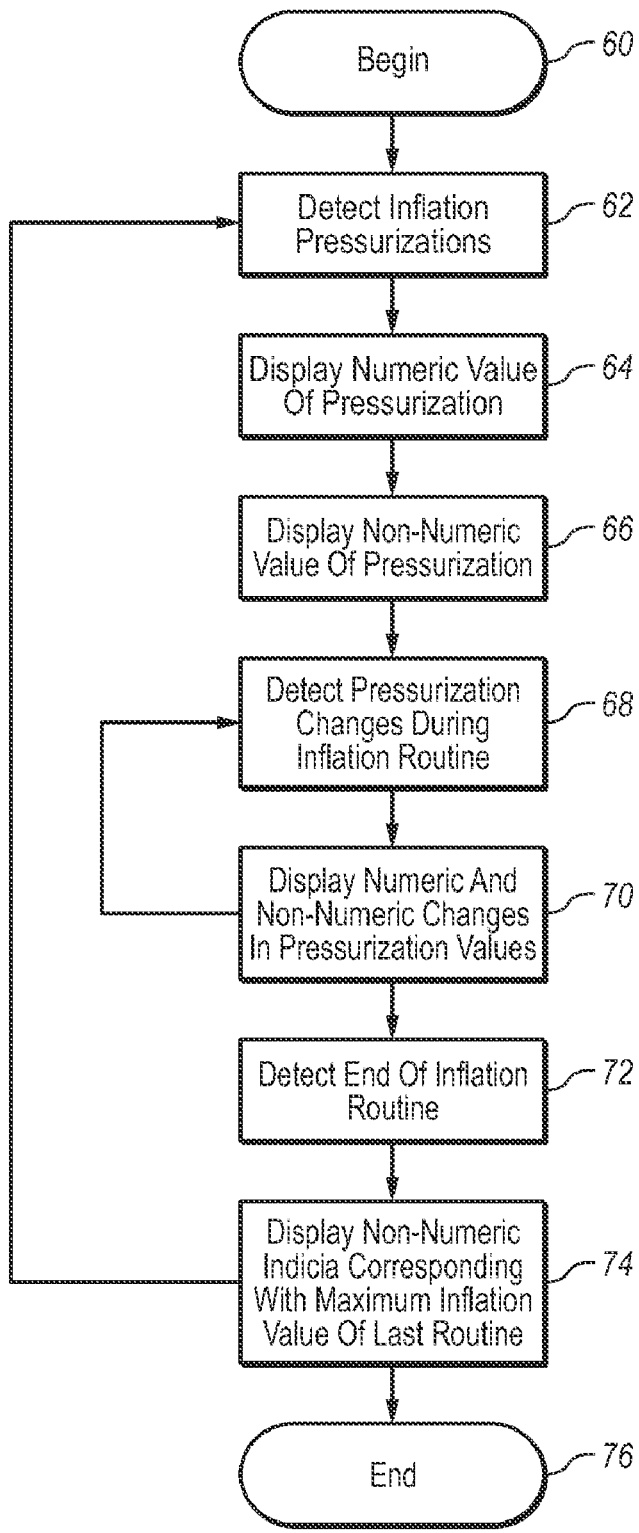
FIG. 4 is a flow chart illustrating of a method of displaying pressurization information utilizing numeric and non-numeric indicia.

FIG. 4 is flow chart depicting a method of displaying pressurization information utilizing numeric and non-numeric indicia, according to one embodiment of the present invention. In the illustrated embodiment, the method begins at a step 60. An inflation pressurization within the interior of the barrel is detected in a step 62. Subsequent to detecting the inflation pressurization, the numeric value of the pressurization is displayed in a step 64. The non-numeric value of the pressurization is then displayed in a step 66. Once the numeric value of the pressurization is displayed in a step 64 and the non-numeric value of the pressurization is displayed in a step 66, a change in pressurization is detected during an inflation routine in a step 68. Once the change in pressurization is detected during the inflation routine, numeric and non-numeric changes in the pressurization values are displayed in a step 70.

Subsequent to detecting of pressurization changes and display of numeric and non-numeric changes in pressurization values during steps 68 and 70, a subsequent change in pressurization may be detected. In the event that a change in pressurization is detected during the inflation routine, step 68 is repeated. Once a change in pressurization is detected and step 68 is repeated, numeric and non-numeric changes in the pressurization values are again displayed in step 70. An end of the inflation routine is detected in a step 72. Once the end of an inflation routine is detected, non-numeric indicia corresponding to a last maximum inflation value of the previous inflation routine is displayed in a step 74. Once the last maximum inflation values are displayed, in the event that an inflation pressurization is detected, the method returns to step 62. In the event that an inflation pressurization is not detected, the method ends in a step 76.

The detection of inflation pressurizations may be accomplished by a pressure sensing apparatus, such as a pressure sensing transducer. A display, such as depicted in FIGS. 3A through 3D, may display the numeric value of the pressurization which provides a precise indication of the pressurization value. The display may also display non-numeric indicia as a representation of the value of pressurization. During the inflation routine, the pressure sensing apparatus may detect pressurization changes and then the display may update the numeric indicia and non-numeric indicia to display the changes in pressurization values. Detecting in step 68 and displaying in step 70 changes in pressurization values may occur multiple times during a pressurization routine. The method may also detect the end of the inflation routine and then display non-numeric indicia corresponding to the last value, or the maximum value, of the inflation routine that just ended. According to one embodiment of the present invention, the method may be directed by display circuitry (depicted in FIGS. 1, 2, and 6), and may be implemented in and/or carried out wholly or partially by software and/or hardware components.

Figure 5A:
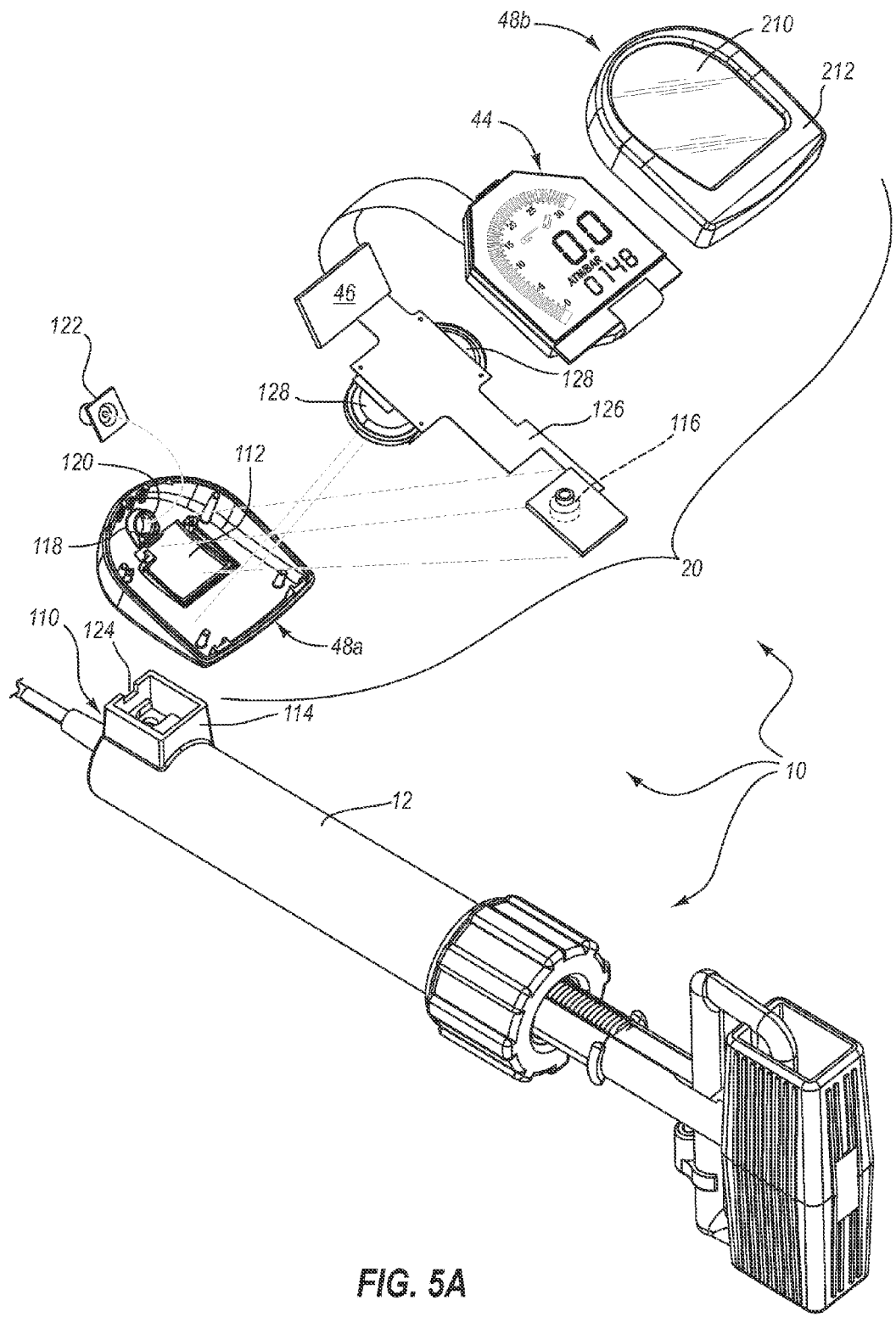
FIG. 5A is an exploded view of the inflation syringe illustrating the modularized component assembly according to one embodiment of the present invention.

FIG. 5A is a perspective view of an inflation syringe 10 illustrating a modularized component assembly of the inflation syringe 10, according to one embodiment of the present invention. In the illustrated embodiment, display 20 comprises separate components as part of the modularized component assembly that allows for testing of the individual components of display 20. By testing individual components of display 20, the cost of manufacturing an inflation syringe of the present disclosure can be reduced because only defective components will be discarded, rather than discarding an entire inflation syringe.

As discussed with reference to FIG. 2, barrel 12 may include a mounting bracket 110 to which display 20 may be attached. The mounting bracket 110 further comprises a securement clip slot 124 for receiving securement bracket 119. Mounting bracket 110, securement bracket slot 124 is an example of a means for attaching the display to a barrel of an inflation syringe. Other examples of means for attaching may include, but are not limited to a clip, hooks and loops, a pin, a detent, a button, or other fastener device.

Display circuitry 46 and display module 44 can be tested separately, assembled, and then placed into display housing base 48b. Display module 44 can comprise numeric and non-numeric indicia to display pressurization information. In the illustrated embodiment, display circuitry 46 is provided in connection with a flexible printed circuit board 126 to aid with assembly of display 20. One or more batteries 128 may also be attached to flexible printed circuit board 126 for convenience during testing and assembly. Flexible printed circuit board 126 is configured to facilitate testing of display circuitry 46 by enabling batteries 128 to power display circuitry 46 during testing.

Display module 44 can be configured to be tested separately and also to be assembled with display circuitry 46 for further testing. During assembly, display circuitry 46 may be removed from flexible printed circuit board 126 and coupled to display module 44. Batteries 128 may also be removed from flexible printed circuit board 126 and installed to power display circuitry 46. The assembly can then be tested together before being placed into display housing base 48b. In another embodiment, flexible printed circuit board 126 can be permanently assembled with display circuitry 46 and display module 44. According to yet another embodiment of the present invention, flexible printed circuit board 126 positions display circuitry 46 and batteries 128 in a desired position. Flexible printed circuit board 126 can then be removed once additional components such as display module 44 and housing 48 are assembled.

A display housing hood 48a is adapted to secure assembled display module 44 and display circuitry 46. Housing hood 48a is configured to receive display module 44 and be coupled to housing base 48b, which may be already mounted to barrel 12. Housing hood 48a and housing base 48b can then be snapped together for easy assembly. Once display 20 is attached to barrel 12, the entire assembled inflation syringe may then be tested. Housing 48 is an example of a means for securing a processing means and a displaying means to an attaching means. Other examples of means for securing may include, but are not limited to a clip, hooks and loops, a pin, a detent, a button, or other fastener device.

Figure 5B:
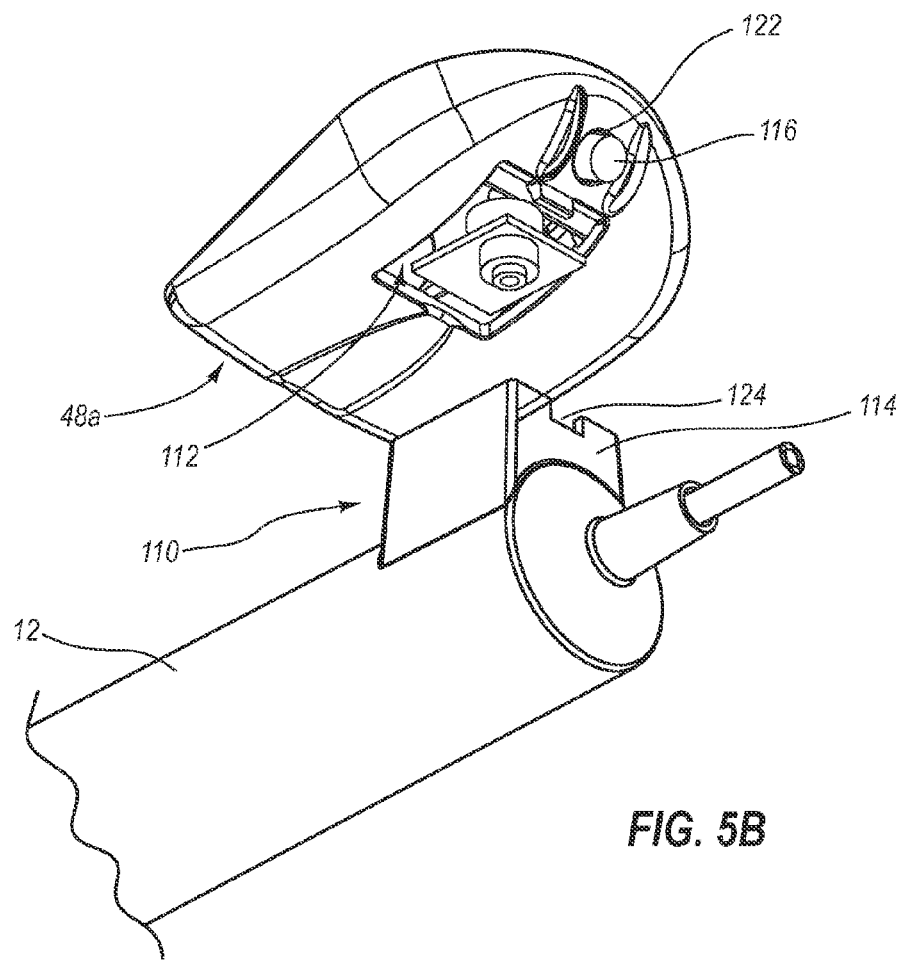
FIG. 5B is perspective view of the housing base and barrel of the inflation syringe illustrating the modularized component assembly according to one embodiment of the present invention.

FIG. 5B is a perspective view illustrating mounting of housing base 48b with barrel 12. In the illustrated embodiment, a housing base 48b and a barrel 12 are depicted. As previously discussed, housing base 48b is configured to be coupled to barrel 12 during assembly of the inflation syringe apparatus. According to one embodiment of the present invention, housing base 48b is coupled to barrel 12 before assembly of the other components of the display 20 (see FIG. 5A). According to alternative embodiments of the present invention, the entire housing 48 of display 20 (see FIG. 5A) are assembled before coupling of housing base 48b to barrel 12.

In the illustrated embodiment, housing base 48b comprises a void 112 and a button receiving bore 118. Barrel 12 comprises a wall 114 and a securement bracket slot 124. In the illustrated embodiment, a pressure sensor 116 is also depicted. During assembly, the user secures housing base 48 to barrel 12 by positioning void 112 over mounting bracket 110 of barrel 12. The user then advances housing base 48b such that wall 114 of mounting bracket 110 slides through void 112. As wall 114 of mounting bracket 110 slides through void 112, wall 114 of mounting bracket 110 is positioned adjacent to void sidewall 113. According to one embodiment of the present invention, the close spatial relationship between void sidewall 113 and wall 114 is provided to minimize lateral movement of housing base 48b relative to mounting bracket 110. When a user has fully advanced housing base 48b such that housing base 48b is positioned adjacent to the bottom portion of mounting bracket 110, securement bracket 119 is positioned within securement bracket slot 124 of mounting bracket 110. In the illustrated embodiment, securement bracket 119 comprises a post which extends a vertical distance away from the underside of housing base 48b. Securement bracket slot 124 comprises a cut-out positioned on the rear side of mounting bracket 110. Securement bracket slot 124 is sized to contact the lateral side portions of securement bracket 119 such that the cooperative engagement between securement bracket 119 and securement bracket slot 124 minimizes or eliminates undesired movement of that housing base 48b relative to mounting bracket 110.

In the illustrated embodiment, a pressure sensor 116 is positioned within mounting bracket 110. The position of mounting bracket 110 and pressure sensor 116 positions pressure sensor 116 in fluid communication with the interior of barrel 12. In this manner, pressure sensor 116 can directly or indirectly monitor and relate information related to the pressurization of the fluid or air positioned within barrel 12.

Mounting bracket 110, securement clip 118, and snap fitting 112 are examples of a means for attaching the display to a barrel of an inflation syringe. Other examples of means for attaching may include, but are not limited to a clip, hooks and loops, a pin, a detent, a button, or other fastener device.

Figure 5C:
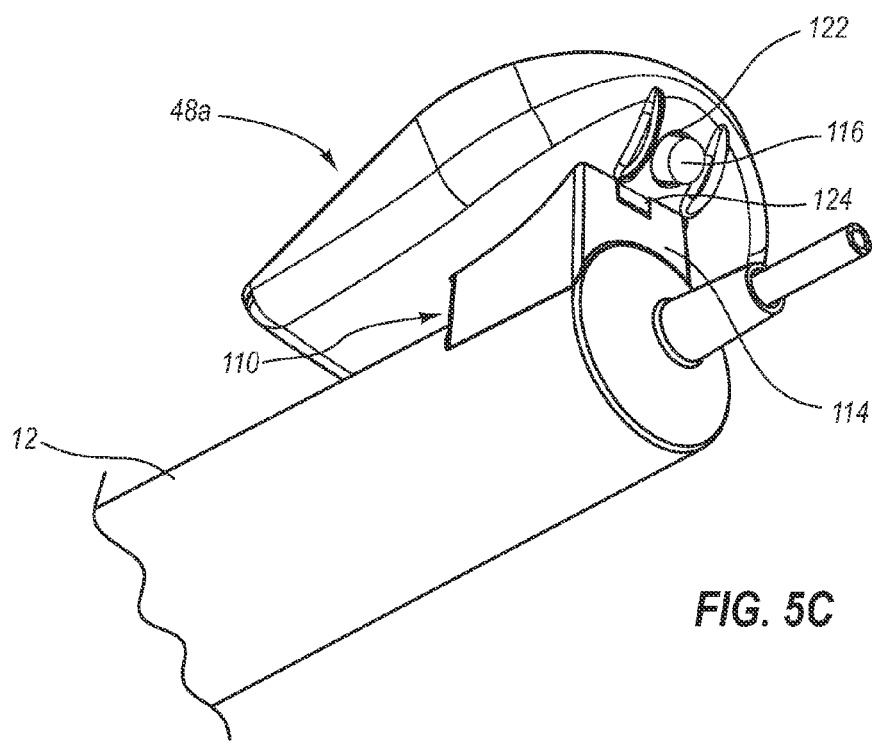
FIG. 5C is perspective view of the housing base and barrel of the inflation syringe illustrating the modularized component assembly according to one embodiment of the present invention.

FIG. 5C illustrates barrel 12 and housing base 48 when housing base has been securely coupled to barrel 12. As can be seen in the illustrated embodiment, when housing base 48 is secured to mounting bracket 110, a button receiving bore 118 is positioned at the distal end of barrel 12 such that a user can freely access and manipulate the button associated with button receiving bore 118. In this manner, a user can actuate the button associated with button receiving bore 118 to control or monitor various aspects of the inflation syringe.

In the illustrated embodiment, wall 114 of mounting bracket 110 has a slight taper such that when a user first slides mounting bracket 110 through void 112 of housing base 48b, a predetermined amount of clearance is provided between wall 114 of mounting bracket 110 and sidewall 113 of void 112. As a user continues to advance housing base 48b in the direction of barrel 12, the clearance between wall 114 and sidewall 113 is decreased until the point in which full contact is provided on all four lateral sides of wall 114 and void sidewall 113. In this manner, pressure or contact in any direction will not create inadvertent or undesired movement of housing base 48b relative to barrel 12.

As will be appreciated by those skilled in the art, a variety of types and combinations of mechanisms for mounting the housing to the barrel can be utilized without departing from the scope and spirit of the present invention. For example, in one embodiment, the mounting bracket is provided in connection with the housing base and a void is provided in connection with the barrel. In another embodiment, the mounting bracket has a circular or elliptical configuration and the void has a circular or elliptical configuration to mate with the shape of the mounting bracket. In yet another embodiment, the pressure sensor is provided at a location other than the mounting bracket. In yet another embodiment, the plurality of mounting brackets or clip-type components are provided to secure the housing to the barrel.

Figure 6A:
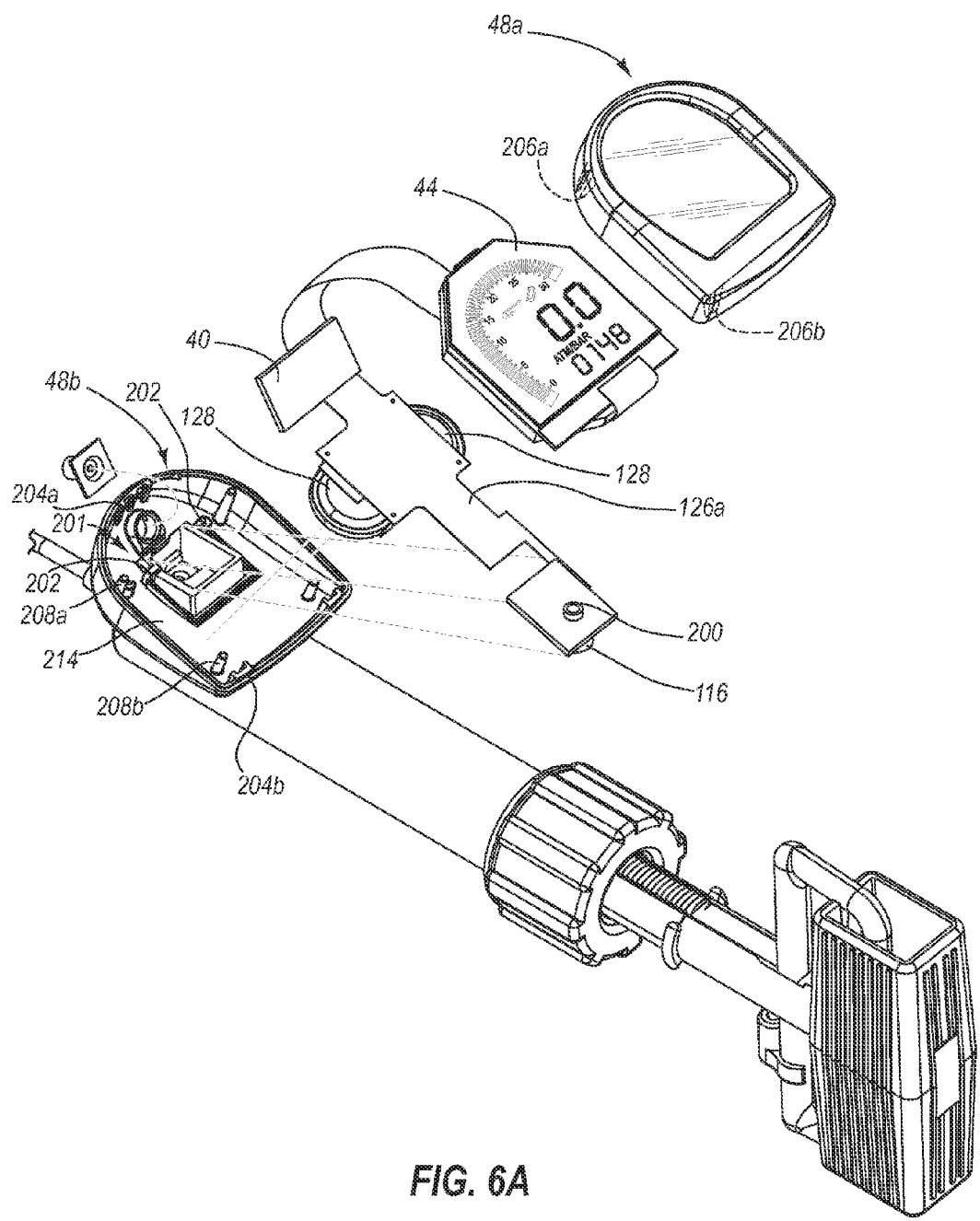
FIG. 6A is an exploded view of the display of the inflation syringe illustrating the modularized component assembly according to one embodiment of the present invention.

FIG. 6A is a perspective view of components of display 20 illustrating assembly of the components of display 20 according to one embodiment of the present invention. In the illustrated embodiment, housing 48 (see FIG. 5A) comprises a housing hood 48a and a housing base 48b. Further, display 20 includes a display module 44, display circuitry 46, pressure sensor 116, flexible printed circuit board 126a and 126b, and batteries 128. In the illustrated embodiment, display module 44 and display circuitry 46 can be tested separately from one another before or after coupling of display circuitry 46 to display module 44. In this manner, in the event that one or more components of the display 20 are faulty, the individual component can be discarded without needing to discard the other viable and usable components of display 20. In the illustrated embodiment, display module 44, display circuit 46, and pressure sensor 116 are coupled together utilizing flexible printed circuit board 126a and 126b. Additionally, in the illustrated embodiment, batteries 128 are secured to flexible printed circuit board 126a. By securing display module 44, display circuitry 46, and securement bracket 119 utilizing flexible printed circuit board 126, each of display module 44, display circuitry 46, and pressure sensor 116 can be positioned in their desired position within housing base 48b and housing hood 48a during assembly of housing hood 48a and housing base 48b while allowing desired coupling of housing base 48b to housing hood 48a.

In the illustrated embodiment, housing base includes a seat 201, a retainment clip 202, a coupling mechanism component 204a and 204b, securement post 208a and 208b, and receptacle 214. Seat 201 is adapted to receive one or both of pressure sensor 116 and display circuitry 46. In the illustrated embodiment, pressure sensor 116 is positionable within void 112 of housing base 48b such that pressure sensor 116 can be received within the mounting bracket 110 of barrel 12 (see FIG. 5B). In the illustrated embodiment, a retainment clip 202 is provided in connection with seat 201. Retainment clip 202 is positioned such that the bottom edge of display circuitry 46 can be positioned beneath retainment clip 202. In this manner, the bottom edge of the display circuitry 46 is positioned between retainment clip 202 and the back surface or bottom surface of housing base 48b. Once the bottom edge of display circuitry 46 is positioned between retainment clip 202 and the bottom of housing base 48b, the display circuitry 46 can be secured within housing base 48b.

Coupling mechanism components 404a, b are adapted to be secured to components of housing hood 48a to secure housing base to housing hood 48a. Additionally, securement posts 208a, b are adapted to help maintain clearance between the walls of housing hood 48a and housing base 48b while also providing a supplemental mechanism for securing housing hood 48a to housing base 48b. Receptacle 214 provides an open area within the volume provided by housing base 48b within which components of display 20 can be positioned. In the illustrated embodiment, receptacle 214 is adapted to receive flexible printed circuit board 126a and batteries 128. Additionally, pressure sensor 116 and display circuitry 46 can be positioned within receptacle 214.

In the illustrated embodiment, housing hood 48a includes coupling mechanism components 206a, b. Coupling mechanism components 206a and 206b are adapted to be secured to coupling mechanism components 204a and 204b of housing base 48b.

As will be appreciated by those skilled in the art, a variety of types and configurations of display components can be provided without departing from the scope and spirit of the present invention. For example, in one embodiment, the housing hood and housing base are provided as one integrated component. In another embodiment, housing base is integrally coupled to housing hood. In yet another embodiment, two or more of the components, including display module 44, display circuitry 46, batteries 128, and flexible printed circuit boards 126 are provided separately and are coupled together once they are positioned within the components of housing hood and housing base. In yet another embodiment, the flexible printed circuit board or other wiring or circuitry to connect components of display 20 are integrated within the housing hood and housing base rather than being provided separately.

Figure 6B:
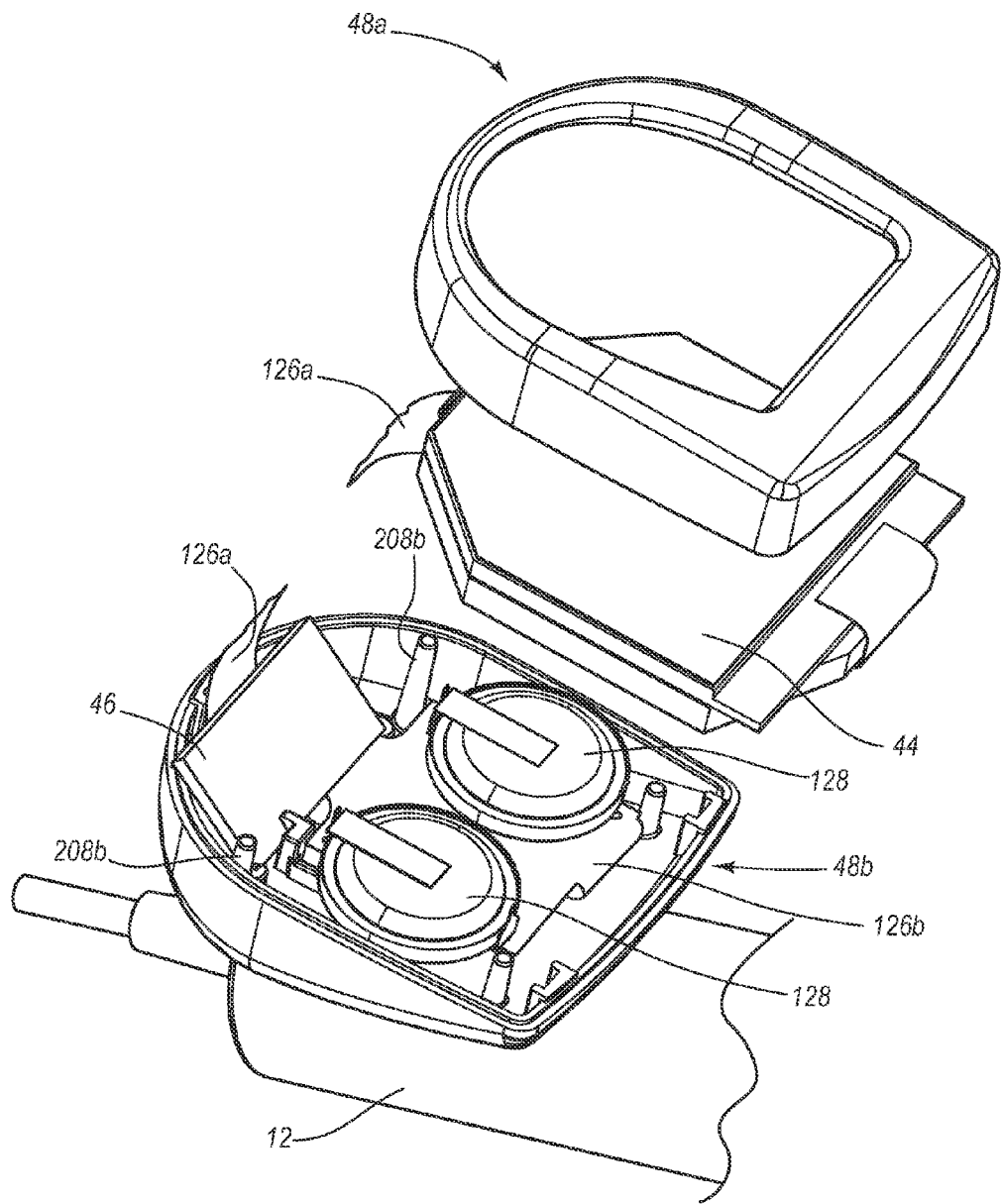
FIG. 6B is exploded perspective view of the display of the housing base and barrel of the inflation syringe illustrating the modularized component assembly according to one embodiment of the present invention.

FIG. 6B is a perspective of the components of housing 20 according to one embodiment of the present invention. In the illustrated embodiment, a display module 44 has been secured within housing hood 48a. Additionally, the pressure sensor 116 has been threaded through void 112 of housing base 48b such that flexible printed circuit board 126a, and 126b are threaded between housing base 48b and housing hood 48a. In this manner, the display module 44 can remain operably connected to display circuitry 46 and pressure sensor 116 while mounting display module 44 within housing hood 48a and mounting sensor 116 through housing base 48b. Additionally, because batteries 128 are secured to flexible printed circuit board 126 and display circuitry 46 is operably connected to flexible printed circuit board 126a and flexible printed circuit board 126b, display module 44 can be actuated and tested in combination with display 46 during assembly.

Figure 6C:
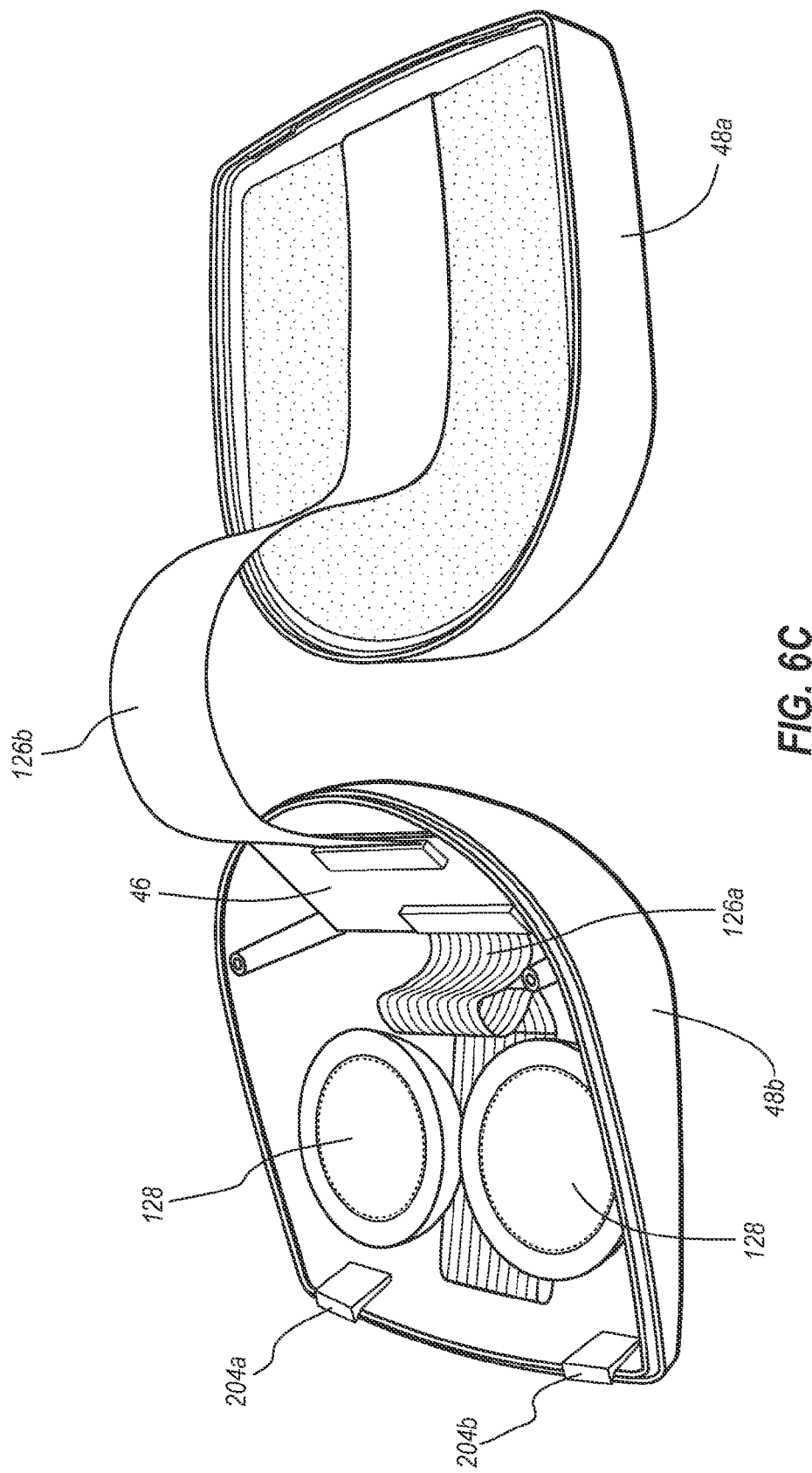
FIG. 6C is perspective view of components of the housing of the display illustrating the modularized component assembly according to one embodiment of the present invention.

FIG. 6C illustrates the components of display 20 during assembly of the components of display 20 according to one embodiment of the present invention. In this illustrated embodiment, display circuitry 46 has been positioned within seat 201 such that a leading edge of display circuitry 46 is positioned beneath retainment clip 202. Flexible printed circuit board 126a has been folded such that pressure sensor 116 (not shown) is positioned through a void 112 (not shown) of housing base 48b. This positions batteries 128 in their desired position within receptacle 214 of housing base 48b. Additionally, this allows for the proper positioning of display circuitry 46 within seat 201.

According to one embodiment of the present invention, the pressure sensor 116 is positioned through void 112 (see FIG. 6B). The length of flexible printed circuit board 126a positioned between batteries 128 and pressure sensor 116 is folded such that batteries 128 are positioned facing upward. The length of flexible printed circuit board 126 positioned between batteries and display circuitry 46 is folded such that batteries 128 are positioned upward and display circuitry 46 is positioned at the portion of housing base 48b and associated with seat 201. Once display circuitry 46 is positioned within seat 201, a length of flexible printed circuit board 126 can be slightly bended or folded to accommodate for the shortened distance between batteries 128 and display circuitry 46. In other words, as display circuitry 46 is positioned beneath retainment clip 202, the displacement between batteries 128 and displace circuitry 46 is lessened. The configuration of flexible printed circuit board 126a allows for subtle folding or other manipulation needed to accommodate for such changes in the juxtaposition of display circuitry 46 and batteries 128.

In the illustrated embodiment, display module is secured within housing hood 48a. Flexible printed circuit board 126b is secured to display module 44 and display circuitry 46. The length of flexible printed circuit board 126b allows for a desired separation between both housing hood 48a and housing base 48b while maintaining the connection between display module 44 and display circuitry 46. In this manner, when display module 44 is positioned within housing hood 48 and display circuitry 46 is positioned within housing base 48b, the components can remain operably connected to one another while also allowing ongoing assembly of the components. In the illustrated embodiment, the coupling provided by flexible printed circuit board 126b also allows for testing of display circuitry 46 and display module 44 while operably connected to one another before final assembly of all the components of display 20. When a user desires to finalize assembly of housing hood 48a and housing base 48b, flexible printed circuit board 126b can be folded such that flexible printed circuit board 126b is positioned between batteries 128 and display module 44 in a sandwich configuration while being entirely positioned within housing hood 48a and housing base 48b. This provides both improved testing of the components of the display 20 while also allowing for improved reliability and efficiency of manufacture of the components of display 20.

It will be appreciated by those skilled in the art that a variety of types and configurations of securement of the components of display 20 can be utilized without departing from the scope and spirit of the present invention. For example, according to one embodiment of the present invention, a single length of flexible printed circuit board can be utilized to secure two or more components of the display. According to another embodiment, the batteries are secured to the other components of the display without utilizing flexible printed circuit board. According to yet another embodiment of the present invention, one or more components of the display are operably secured to one another when the housing hood is secured to the housing base.

Figure 6D:
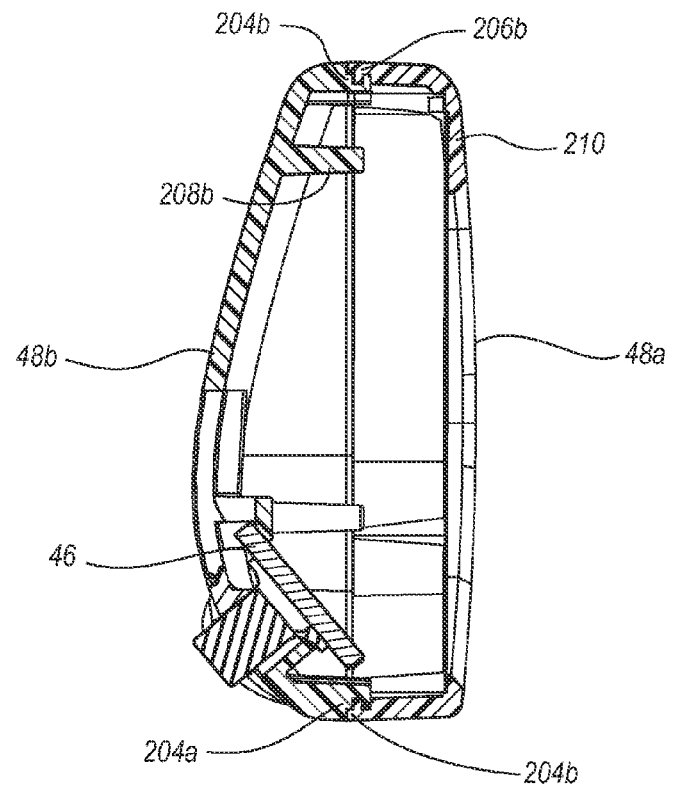
FIG. 6D is a side cut-away view of the housing of the display illustrating the modularized component assembly according to one embodiment of the present invention.

FIG. 6D is a side cross-sectional view of display 20 illustrating the juxtaposition of housing hood 48a and housing base 48b after assembly of an inflation syringe. In the illustrated embodiment, housing base 48b is secured to housing hood 48a securing the position of display circuitry 46 within housing 48. In the illustrated embodiment, housing base is secured to housing hood by the securement of coupling mechanism components 204a, b to coupling mechanism components 206a, b. Coupling mechanism components 204a, b are associated with housing base 48b. Coupling mechanism components 206a, b are associated with housing hood 48a. Additionally, according to one embodiment of the present invention, securement posts 208a, b are utilized to secure housing hood 48a to housing base 48b. In the illustrated embodiment, display module 44, pressure sensor 116, flexible printed circuit board 126a and flexible printed circuit board 126b are not shown. However, as previously discussed, the display module, pressure sensor, and flexible printed circuit boards are adapted to be operably connected within housing hood 48a and housing base 48b.

Figure 6E:
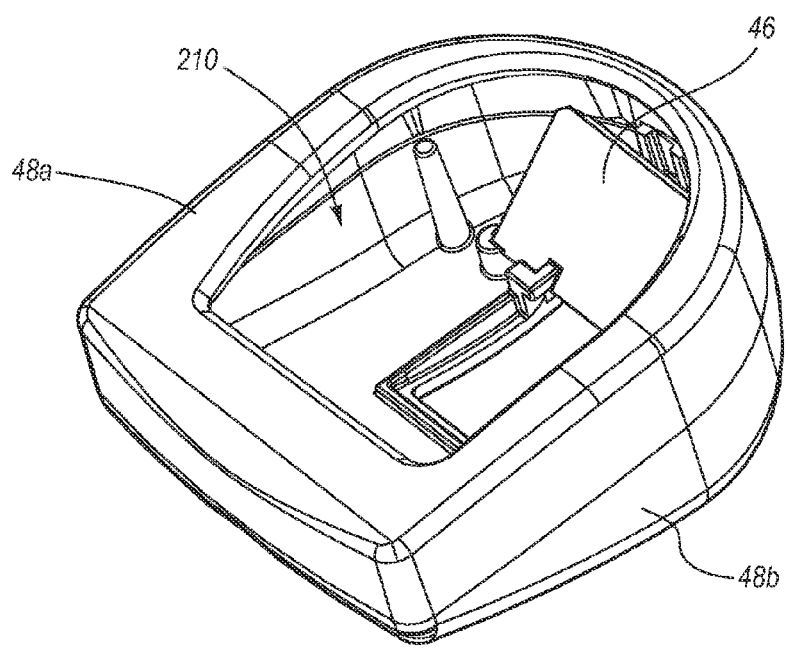
FIG. 6E is perspective view of components of the housing of the display illustrating the modularized component assembly according to one embodiment of the present invention.

FIG. 6E is a perspective view illustrating housing hood 48a and housing base 48b when housing hood 48a is secured to housing base 48b. In the illustrated embodiment, no display module is shown within housing hood 48a for the purpose of illustrating the juxtaposition of the housing hood, 48a, housing base 48b and display circuitry 46. In this manner, the user can observe the manner in which display circuitry 46 is secured utilizing retainment clip 202. In the illustrated embodiment, clip 202 is positioned adjacent void 112 in housing base 48b. A user advances display circuitry 46 such that a leading edge of display circuitry 46 is positioned beneath retainment clip 202. Once display circuitry 46 is positioned relative to retainment clip 202, display circuitry 46 can be secured within housing base 48b. In one embodiment, display circuitry 46 is secured within seat 201 by the cooperative engagement of housing hood 48a and housing base 48b. According to another embodiment of the present invention, the components of housing base 48b alone secure display circuitry 46. In another embodiment, once display circuitry 46 is positioned relative to retainment clip 202, display circuitry is welded, glued, or otherwise secured mechanically to housing base 48b. In the illustrating embodiment, display circuitry 46 is positioned at an angle within housing base 48b by being positioned at a sloped angle relative to the other components of housing base 48b. Flexible printed circuit board, batteries, or other components to be positioned within receptacle 214 of housing base 48b can be positioned in a desired manner without impedance from or interference to display circuitry 46.

As will be appreciated by those skilled in the art, a variety of types and configurations of housings can be provided without departing from the scope and spirit of the present invention. For example, in one embodiment of the present invention, a mechanism other than a retainment clip is utilized to secure the display circuitry. In another embodiment, the display circuitry is positioned within its own receptacle to protect it from damage from the other components of the display. In yet another embodiment, the display circuitry is positioned away from the void of the housing base to protect the display circuitry from the external environment.

Modularized component assembly, and testing of individual and assembled components during the assembly, enable identification of defective components. Consequently, significant cost reduction may be achieved simply by discarding only defective components rather than discarding entire inflation syringes which may include several inflation syringe components which are not defective.

Figure 7:
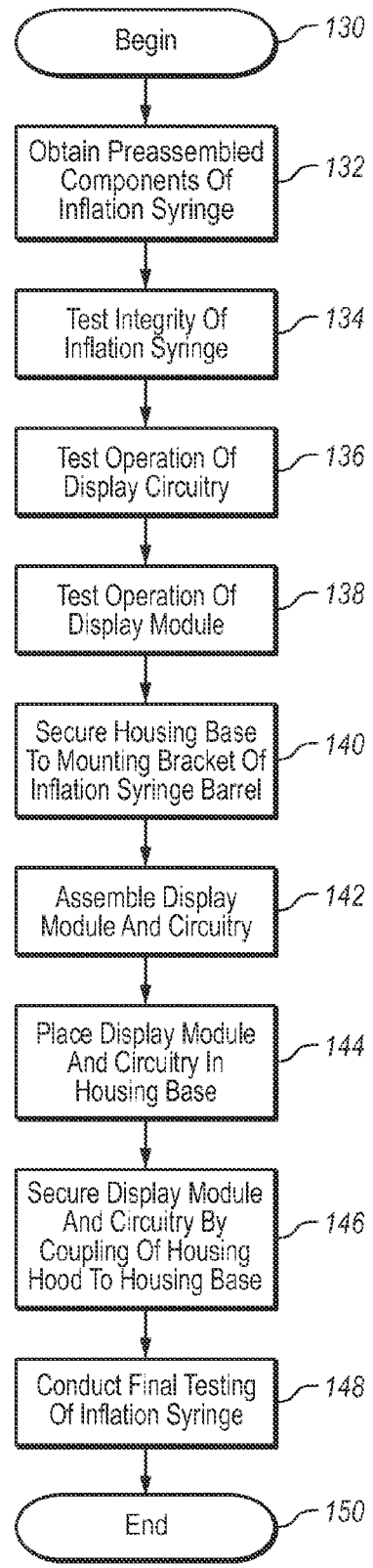
FIG. 7 is a flow chart illustrating a method of testing and assembling an inflation syringe utilizing a modularized component assembly.

FIG. 7 is a flow chart illustrating a method of testing and assembling an inflation syringe utilizing a modularized component assembly, according to one embodiment of the present invention. The method begins at a step 130. The components of the inflation syringe are obtained in a step 132. Once the components of the inflation syringe are obtained, the integrity of the inflation syringe barrel is tested in a step 134. The operation of the display circuitry is then tested in a step 134. Once the operation of the display circuitry is tested, the operation of the display module is tested in a step 138.

The housing base is then secured to the mounting bracket of the inflation syringe in a step 140. Once the housing base is secured to the mounting bracket, the display module and circuitry are assembled in a step 142. The display module and circuitry are placed in the housing base in a step 144. Once the display module and circuitry are placed in the housing base, the housing hood is coupled to the housing base to secure the display module and circuitry to the inflation syringe in a step 146. The assembled inflation syringe including the assembled display then undergoes final testing in a step 148. Once the assembled inflation syringe has undergone final testing, the method is ended in a step 150.

According to one embodiment of the present invention, the preassembled components may include, but are not limited to, a pre-assembled syringe system comprising a barrel and plunger, a display housing comprising a base and a hood, a display module, and display circuitry. In another embodiment, a tubing may be pre-connected to the barrel with the tubing being adapted to connect to an inflatable medical device. Each of the components of the inflation syringe may be tested separately. The method may test the integrity of the syringe system, including the barrel and plunger and any other syringe system components to ensure a fluid tight seal and to ensure that the barrel can be pressurized and hold pressurization. According to one embodiment of the present invention, the testing method is adapted to test operation of the display circuitry and test operation of the display module, including testing of both the numeric and non-numeric indicia.

After verifying that the components of the inflation syringe function properly, modularized assembly may begin by securing the housing base to the mounting bracket of the inflation syringe barrel. The display module and display circuitry may then be assembled and tested together before being installed. If the display module and display circuitry properly function when assembled, the assembly may be placed in the display housing base. The display module and display circuitry may be secured by coupling the housing hood to the housing base. When the display attached to the syringe barrel, the fully assembled inflation syringe can be tested.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. Note that elements recited in means-plus-function format are intended to be construed in accordance with 35 U.S.C. §112 ¶6.

What is claimed is:

1. A modularized component assembly for an inflation syringe comprising:
    a barrel defining an inner lumen, the barrel configured to hold a desired inflation pressure;
    a plunger configured to be received within the inner lumen of the barrel to increase pressurization within the barrel;
    a sensor apparatus for sensing inflation pressurization within the barrel;
    a display processor to process signals received from the sensor apparatus;
    a display module coupled to the display processor to display information contained in the signals from the sensor apparatus, wherein the display module comprises a numeric indicator which provides a numeric indication of a current inflation pressurization within the barrel and a pluarlity of non-numeric indicia which are actuated in a progressive manner, such that non-numeric indicia representing values less than the current inflation pressurization value remain actuated as the pressurization within the barrel increases and decreases;
    a display housing comprising a base and a hood, wherein the base is configured to attach to the barrel and to receive the display processor and display module, and wherein the display hood is configured to couple to the display base and secure the display processor and display module within the display housing.

2. The modularized component assembly for an inflation syringe of claim 1, wherein the sensor apparatus is configured to be tested to determine operability of the sensor independent of the barrel, the plunger, the display processor, the display module, and the display housing of the modularized component assembly.

3. The modularized component assembly for an inflation syringe of claim 1, wherein the display processor is configured to be tested to determine operability of the sensor independent of the barrel, the plunger, the sensor apparatus, the display module, and the display housing of the modularized component assembly.

4. The modularized component assembly for an inflation syringe of claim 1, wherein the display module is configured to be tested to determine operability of the sensor independent of the barrel, the plunger, the sensor apparatus, the display processor, and the display housing of the modularized component assembly.

5. The modularized component assembly for an inflation syringe of claim 1, wherein the barrel is configured to be tested to determine operability of the sensor independent of the sensor apparatus, the display processor, the display module, and the display housing of the modularized component assembly.

6. The modularized component assembly for an inflation syringe of claim 1, wherein two or more of the sensor apparatus, the display processor and the display module are configured to be tested together to determine operability of the sensor apparatus, independent of the barrel, the plunger, and the display housing of the modularized component assembly.

7. The modularized component assembly for an inflation syringe of claim 1, wherein one or more batteries utilized to provide power to one or more of the sensor apparatus, the display processor, and the display module of the modularized component assembly are flexibly coupled to one or both of the display module and the display processor for proper placement of the batteries in connection with one or both of the display module and the display processor within the housing hood and the housing base.

8. The modularized component assembly for an inflation syringe of claim 1, wherein the display processor and the display module can be positioned between the housing hood and the housing base.

9. The modularized component assembly for an inflation syringe of claim 8, wherein the sensor apparatus, the display processor, and the display module are secured to the barrel of the inflation syringe by the housing hood and the housing base.

10. The modularized component assembly for an inflation syringe of claim 9, wherein when the housing hood and the housing base are secured to the barrel of the inflation syringe, the display processor is operably connected to the sensor apparatus.

* * * * *